US011168287B2

(12) United States Patent
Engelbrecht et al.

(10) Patent No.: US 11,168,287 B2
(45) Date of Patent: Nov. 9, 2021

(54) ANTI-ADHERENT COMPOSITIONS AND METHODS OF INHIBITING THE ADHERENCE OF MICROBES TO A SURFACE

(71) Applicant: Kimberly-Clark Worldwide, Inc., Neenah, WI (US)

(72) Inventors: Kathleen C. Engelbrecht, Kaukauna, WI (US); Stacy A. Mundschau, Weyauwega, WI (US); David W. Koenig, Menasha, WI (US); Scott W. Wenzel, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 16/301,580

(22) PCT Filed: May 26, 2016

(86) PCT No.: PCT/US2016/034252
§ 371 (c)(1),
(2) Date: Nov. 14, 2018

(87) PCT Pub. No.: WO2017/204806
PCT Pub. Date: Nov. 30, 2017

(65) Prior Publication Data
US 2019/0177667 A1    Jun. 13, 2019

(51) Int. Cl.
| | | |
|---|---|---|
| *C11D 3/48* | (2006.01) | |
| *C11D 17/04* | (2006.01) | |
| *C11D 3/37* | (2006.01) | |
| *C11D 3/20* | (2006.01) | |
| *C11D 3/26* | (2006.01) | |
| *A61K 8/02* | (2006.01) | |
| *A61K 8/88* | (2006.01) | |
| *A61K 8/81* | (2006.01) | |
| *A61K 8/85* | (2006.01) | |
| *A61K 8/86* | (2006.01) | |
| *A61K 8/90* | (2006.01) | |
| *A61K 8/37* | (2006.01) | |
| *A61K 8/40* | (2006.01) | |
| *A61Q 17/00* | (2006.01) | |

(Continued)

(52) U.S. Cl.
CPC ................ *C11D 3/48* (2013.01); *A01N 25/00* (2013.01); *A01N 25/08* (2013.01); *A01N 31/02* (2013.01); *A01N 37/02* (2013.01); *A01N 37/06* (2013.01); *A01N 37/34* (2013.01); *A01N 37/42* (2013.01); *A01N 43/50* (2013.01); *A61K 8/0208* (2013.01); *A61K 8/37* (2013.01); *A61K 8/40* (2013.01); *A61K 8/8152* (2013.01); *A61K 8/85* (2013.01); *A61K 8/86* (2013.01); *A61K 8/88* (2013.01); *A61K 8/90* (2013.01); *A61K 9/0014* (2013.01); *A61K 9/06* (2013.01); *A61K 47/32* (2013.01); *A61K 47/34* (2013.01); *A61Q 17/005* (2013.01); *A61Q 19/10* (2013.01); *C08L 71/02* (2013.01); *C11D 3/2079* (2013.01); *C11D 3/2086* (2013.01); *C11D 3/2093* (2013.01); *C11D 3/26* (2013.01); *C11D 3/3707* (2013.01); *C11D 3/3715* (2013.01); *C11D 3/3757* (2013.01); *C11D 3/3765* (2013.01); *C11D 3/3769* (2013.01); *C11D 17/049* (2013.01); *C08G 2650/58* (2013.01)

(58) Field of Classification Search
None
See application file for complete search history.

(56) References Cited

U.S. PATENT DOCUMENTS

| | | |
|---|---|---|
| 1,680,584 A | 8/1928 | Angell et al. |
| 3,241,898 A | 3/1966 | Propst |
| | (Continued) | |

FOREIGN PATENT DOCUMENTS

| | | |
|---|---|---|
| AU | 2010226857 B2 | 7/2016 |
| AU | 2015297023 B2 | 11/2019 |
| | (Continued) | |

OTHER PUBLICATIONS

Datasheet for WetFilm™ by Inolex (downloaded Sep. 14, 2019 from https://inolexcosmetics.ulprospector.com/en/na/PersonalCare/Detail (Year: 2019).*

(Continued)

*Primary Examiner* — Michael P Cohen
(74) *Attorney, Agent, or Firm* — Kimberly-Clark Worldwide, Inc.

(57) ABSTRACT

Methods of inhibiting microbes from attaching to a surface and anti-adherent compositions are disclosed. One method can include providing an anti-adherent composition that includes an anti-adherent agent configured to inhibit microbes from attaching to the surface. The anti-adherent agent can be: Acrylates Copolymer, Trimethylpentanediol/Adipic Acid/Glycerin crosspolymer, Trimethylpentanediol/Adipic Acid Copolymer, Ethylhexyl Stearate, Ethylhexyl Salicylate, Acrylates/C12-22 Alkylmethacrylate Copolymer, Octocrylene, Ethylene Oxide/Propylene Oxide Block Copolymer, Polyquaternium-101, or any combinations thereof. The method can include applying the composition to the surface and allowing at least some of the composition to remain on the surface such that the anti-adherent agent inhibits microbes from attaching to the surface. The anti-adherent composition can include a humectant and can be non-antimicrobial.

10 Claims, No Drawings

(51) Int. Cl.
*A01N 25/08* (2006.01)
*A01N 43/50* (2006.01)
*A01N 37/02* (2006.01)
*A01N 37/06* (2006.01)
*A01N 37/34* (2006.01)
*A01N 37/42* (2006.01)
*A01N 31/02* (2006.01)
*A01N 25/00* (2006.01)
*C08L 71/02* (2006.01)
*A61K 47/34* (2017.01)
*A61K 9/00* (2006.01)
*A61K 47/32* (2006.01)
*A61K 9/06* (2006.01)
*A61Q 19/10* (2006.01)

(56) References Cited

U.S. PATENT DOCUMENTS

| | | | |
|---|---|---|---|
| 3,303,048 A | 2/1967 | Cooper et al. | |
| 3,338,992 A | 8/1967 | Kinney et al. | |
| 3,341,394 A | 9/1967 | Kinney et al. | |
| 3,494,821 A | 2/1970 | Evans et al. | |
| 3,502,538 A | 3/1970 | Petersen et al. | |
| 3,502,763 A | 3/1970 | Hartmann et al. | |
| 3,542,615 A | 11/1970 | Dobo et al. | |
| 3,692,618 A | 9/1972 | Carduck et al. | |
| 3,802,817 A | 4/1974 | Goto et al. | |
| 3,849,241 A | 11/1974 | Butin et al. | |
| 3,954,962 A | 5/1976 | Prussin | |
| 4,007,113 A | 2/1977 | Ostreicher | |
| 4,100,324 A | 7/1978 | Anderson et al. | |
| 4,144,370 A | 3/1979 | Boulton | |
| 4,340,563 A | 7/1982 | Appel et al. | |
| 4,361,486 A | 11/1982 | Hou et al. | |
| 4,624,890 A | 11/1986 | Lloyd et al. | |
| 4,795,668 A | 1/1989 | Krueger et al. | |
| 5,057,361 A | 10/1991 | Sayovitz et al. | |
| 5,057,368 A | 10/1991 | Largman et al. | |
| 5,069,970 A | 12/1991 | Largman et al. | |
| 5,108,820 A | 4/1992 | Kaneko et al. | |
| 5,162,074 A | 11/1992 | Hills | |
| 5,277,976 A | 1/1994 | Hogle et al. | |
| 5,284,703 A | 2/1994 | Everhart et al. | |
| 5,336,552 A | 8/1994 | Strack et al. | |
| 5,350,624 A | 9/1994 | Georger et al. | |
| 5,382,400 A | 1/1995 | Pike et al. | |
| 5,413,789 A * | 5/1995 | Hagiwara | A01N 25/10 424/401 |
| 5,466,410 A | 11/1995 | Hills | |
| 5,512,186 A | 4/1996 | Wright et al. | |
| 5,593,599 A | 1/1997 | Wright et al. | |
| 5,736,058 A | 4/1998 | Wright et al. | |
| 5,742,943 A | 4/1998 | Chen | |
| 5,785,179 A | 7/1998 | Buczwinski et al. | |
| 5,855,788 A | 1/1999 | Everhart et al. | |
| 5,908,707 A | 6/1999 | Cabell et al. | |
| 5,935,883 A | 8/1999 | Pike | |
| 5,942,219 A | 8/1999 | Hendriks | |
| 5,951,965 A | 9/1999 | Ansari et al. | |
| 5,964,351 A | 10/1999 | Zander | |
| 5,989,004 A | 11/1999 | Cook | |
| 5,989,527 A | 11/1999 | Siegried et al. | |
| 6,030,331 A | 2/2000 | Zander | |
| 6,110,381 A | 8/2000 | Wright | |
| 6,123,996 A | 9/2000 | Larsson et al. | |
| 6,158,614 A | 12/2000 | Haines et al. | |
| 6,180,584 B1 | 1/2001 | Sawan et al. | |
| 6,200,669 B1 | 3/2001 | Marmon et al. | |
| 6,231,719 B1 | 5/2001 | Garvey et al. | |
| 6,241,898 B1 | 6/2001 | Wright et al. | |
| 6,248,880 B1 | 6/2001 | Karlson | |
| 6,267,996 B1 | 7/2001 | Bombardelli et al. | |
| 6,269,969 B1 | 8/2001 | Huang et al. | |
| 6,269,970 B1 | 8/2001 | Huang et al. | |
| 6,273,359 B1 | 8/2001 | Newman et al. | |
| 6,274,041 B1 | 8/2001 | Williamson et al. | |
| 6,294,186 B1 | 9/2001 | Beerse et al. | |
| 6,306,514 B1 | 10/2001 | Weikel et al. | |
| 6,315,864 B2 | 11/2001 | Anderson et al. | |
| 6,340,663 B1 | 1/2002 | Deleo et al. | |
| 6,515,095 B1 | 2/2003 | Omura et al. | |
| 6,565,749 B1 | 5/2003 | Hou et al. | |
| 6,569,828 B1 | 5/2003 | Thomas et al. | |
| 6,630,016 B2 | 10/2003 | Koslow | |
| 6,639,066 B2 | 10/2003 | Boström et al. | |
| 6,696,070 B2 | 2/2004 | Dunn | |
| 6,770,204 B1 | 8/2004 | Koslow | |
| 6,800,354 B2 * | 10/2004 | Baumann | B08B 17/06 428/141 |
| 6,838,005 B2 | 1/2005 | Tepper et al. | |
| 6,916,480 B2 | 7/2005 | Anderson et al. | |
| 6,946,196 B2 | 9/2005 | Foss | |
| 7,169,304 B2 | 1/2007 | Hughes et al. | |
| 7,192,601 B2 | 3/2007 | Walker | |
| 7,287,650 B2 | 10/2007 | Koslow | |
| 7,288,513 B2 | 10/2007 | Taylor et al. | |
| 7,384,762 B2 | 6/2008 | Drocourt et al. | |
| 7,432,234 B2 | 10/2008 | Ochomogo et al. | |
| 7,569,530 B1 | 8/2009 | Pan et al. | |
| 7,576,256 B2 | 8/2009 | Björnberg et al. | |
| 7,625,844 B1 | 12/2009 | Yang et al. | |
| 7,642,395 B2 | 1/2010 | Schroeder et al. | |
| 7,795,199 B2 | 9/2010 | Molinaro et al. | |
| 7,872,051 B2 | 1/2011 | Clarke | |
| 7,985,209 B2 | 7/2011 | Villanueva et al. | |
| 7,993,675 B2 | 8/2011 | Oliver et al. | |
| 8,030,226 B2 | 10/2011 | Bradley et al. | |
| 8,034,844 B2 | 10/2011 | Fox et al. | |
| 8,293,699 B2 | 10/2012 | Fütterer et al. | |
| 8,318,654 B2 | 11/2012 | Hoffman et al. | |
| 8,343,523 B2 | 1/2013 | Toreki et al. | |
| 8,481,480 B1 | 7/2013 | Lam et al. | |
| 8,506,978 B2 | 8/2013 | Soerens et al. | |
| 8,530,524 B2 | 9/2013 | Wegner et al. | |
| 8,551,518 B2 | 10/2013 | Marsh et al. | |
| 8,603,771 B2 | 12/2013 | Stanley et al. | |
| 8,685,178 B2 | 4/2014 | Do et al. | |
| 8,771,661 B2 | 7/2014 | MacDonald | |
| 8,871,722 B2 | 10/2014 | Harding | |
| 8,877,882 B1 * | 11/2014 | Salamone | C08F 220/20 526/279 |
| 9,006,163 B2 | 4/2015 | Hourigan et al. | |
| 9,034,346 B2 | 5/2015 | Miller et al. | |
| 9,119,779 B2 | 9/2015 | Marsh et al. | |
| 9,226,517 B2 | 1/2016 | Segura et al. | |
| 9,254,255 B2 | 2/2016 | Chang et al. | |
| 9,326,924 B1 | 5/2016 | Fourre et al. | |
| 9,555,141 B2 | 1/2017 | Samadpour | |
| 9,675,717 B2 | 6/2017 | Kim et al. | |
| 9,969,885 B2 | 5/2018 | Engelbrecht et al. | |
| 10,028,899 B2 | 7/2018 | Chaudhary et al. | |
| 10,485,742 B2 | 11/2019 | Patel et al. | |
| 10,792,236 B2 | 10/2020 | Pan et al. | |
| 10,813,948 B2 | 10/2020 | Abbott et al. | |
| 10,960,012 B2 | 3/2021 | Baker et al. | |
| 2001/0037100 A1 | 11/2001 | Shanklin | |
| 2001/0040136 A1 | 11/2001 | Wei et al. | |
| 2001/0046525 A1 | 11/2001 | Bombardelli et al. | |
| 2002/0050016 A1 | 5/2002 | Willman et al. | |
| 2002/0189998 A1 | 12/2002 | Haase et al. | |
| 2003/0008791 A1 | 1/2003 | Chiang | |
| 2003/0044446 A1 | 3/2003 | Moro et al. | |
| 2003/0069317 A1 | 4/2003 | Seitz, Jr. et al. | |
| 2003/0091540 A1 | 5/2003 | Ahmad et al. | |
| 2003/0162684 A1 | 8/2003 | Huyhn et al. | |
| 2004/0009141 A1 | 1/2004 | Koenig et al. | |
| 2004/0024374 A1 | 2/2004 | Hjorth et al. | |
| 2005/0130870 A1 | 6/2005 | Ochomogo et al. | |
| 2005/0137540 A1 | 6/2005 | Villanueva et al. | |
| 2005/0182021 A1 | 8/2005 | Nichols et al. | |
| 2005/0242041 A1 | 11/2005 | Cumberland | |
| 2005/0244480 A1 | 11/2005 | Koenig et al. | |
| 2005/0271595 A1 | 12/2005 | Brown | |

(56) References Cited

U.S. PATENT DOCUMENTS

| | | |
|---|---|---|
| 2006/0008621 A1 | 1/2006 | Gusky et al. |
| 2006/0134239 A1 | 6/2006 | Weide et al. |
| 2006/0140899 A1 | 6/2006 | Koenig et al. |
| 2006/0193789 A1 | 8/2006 | Tamarkin et al. |
| 2006/0204466 A1 | 9/2006 | Littau et al. |
| 2006/0205619 A1 | 9/2006 | Mayhall et al. |
| 2006/0292086 A1 | 12/2006 | Curtis |
| 2007/0020649 A1 | 1/2007 | Tseng et al. |
| 2007/0141934 A1 | 6/2007 | Sayre et al. |
| 2007/0207104 A1 | 9/2007 | Borish |
| 2007/0237800 A1 | 10/2007 | Lahann |
| 2007/0253926 A1 | 11/2007 | Tadrowski et al. |
| 2007/0286894 A1 | 12/2007 | Marsh et al. |
| 2008/0102053 A1 | 5/2008 | Childers |
| 2008/0275113 A1 | 11/2008 | Huetter et al. |
| 2008/0293613 A1 | 11/2008 | Johnson et al. |
| 2008/0293826 A1 | 11/2008 | Rose et al. |
| 2008/0312118 A1 | 12/2008 | Futterer et al. |
| 2009/0004122 A1 | 1/2009 | Modak et al. |
| 2009/0082472 A1 | 3/2009 | Peters |
| 2009/0087465 A1 | 4/2009 | Doney et al. |
| 2009/0155325 A1 | 6/2009 | Wenzel et al. |
| 2009/0155327 A1 | 6/2009 | Martin et al. |
| 2009/0191248 A1 | 7/2009 | Hoffman et al. |
| 2009/0226498 A1 | 9/2009 | Flugge-Berendes et al. |
| 2010/0135916 A1 | 6/2010 | Courel et al. |
| 2010/0297029 A1 | 11/2010 | Biering et al. |
| 2011/0009309 A1 | 1/2011 | Mertens et al. |
| 2011/0081528 A1 | 4/2011 | Shannon et al. |
| 2011/0091393 A1 | 4/2011 | Simmonds et al. |
| 2011/0236447 A1 | 9/2011 | Yoshimura et al. |
| 2011/0293681 A1 | 12/2011 | Berlin et al. |
| 2012/0046362 A1 | 2/2012 | Kawahara et al. |
| 2012/0121459 A1 | 5/2012 | Edgington et al. |
| 2012/0164206 A1 | 6/2012 | Soerens et al. |
| 2012/0207805 A1 | 8/2012 | Colman et al. |
| 2012/0263805 A1 | 10/2012 | Popp |
| 2012/0269912 A1 | 10/2012 | Roberts |
| 2012/0294911 A1 | 11/2012 | Redmond et al. |
| 2013/0037048 A1 | 2/2013 | Edgington et al. |
| 2013/0079733 A1 | 3/2013 | Burt et al. |
| 2013/0209576 A1 | 8/2013 | Brumeister et al. |
| 2013/0274110 A1 | 10/2013 | Westbye et al. |
| 2013/0287724 A1 | 10/2013 | Hoffman et al. |
| 2014/0014584 A1 | 1/2014 | Cone et al. |
| 2014/0030198 A1 | 1/2014 | Fares et al. |
| 2014/0147402 A1 | 5/2014 | Klug et al. |
| 2014/0170089 A1 | 6/2014 | Thaggard |
| 2014/0205546 A1* | 7/2014 | Macoviak ............... A61K 8/29 424/10.3 |
| 2014/0275255 A1 | 9/2014 | Pedersen et al. |
| 2014/0356303 A1* | 12/2014 | Rocco .................. A61K 8/37 424/64 |
| 2015/0010490 A1 | 1/2015 | Kim et al. |
| 2015/0059795 A1 | 3/2015 | Vatter et al. |
| 2015/0265507 A1 | 9/2015 | Norman |
| 2015/0290102 A1 | 10/2015 | Cozean et al. |
| 2015/0352033 A1 | 12/2015 | Hoffman et al. |
| 2016/0051452 A1 | 2/2016 | Nishizawa et al. |
| 2017/0042787 A1 | 2/2017 | Phukan et al. |
| 2017/0208798 A1 | 7/2017 | Chaudhary et al. |
| 2017/0210900 A1 | 7/2017 | Engelbrecht et al. |
| 2017/0224596 A1 | 8/2017 | Chaudhary et al. |
| 2017/0303535 A1 | 10/2017 | Engelbrecht et al. |
| 2017/0367350 A1 | 12/2017 | Koenig et al. |
| 2018/0098536 A1 | 4/2018 | Koenig et al. |
| 2018/0311127 A1 | 11/2018 | Padyachi et al. |
| 2019/0133126 A1 | 5/2019 | Modak et al. |
| 2019/0175464 A1 | 6/2019 | Myers et al. |
| 2019/0177667 A1 | 6/2019 | Engelbrecht et al. |
| 2019/0262254 A1 | 8/2019 | Ansari et al. |
| 2020/0121568 A1 | 4/2020 | Foley |
| 2020/0131454 A1 | 4/2020 | Copeland et al. |
| 2020/0148897 A1 | 5/2020 | Kang et al. |
| 2020/0206277 A1 | 7/2020 | Whitlock et al. |
| 2020/0338139 A1 | 10/2020 | Majeed et al. |
| 2020/0354591 A1 | 11/2020 | Engelbrecht et al. |

FOREIGN PATENT DOCUMENTS

| | | |
|---|---|---|
| AU | 2019204536 B2 | 5/2020 |
| AU | 2019204543 B2 | 5/2020 |
| AU | 2014409811 B2 | 2/2021 |
| BR | 102013009302 A2 | 11/2014 |
| BR | 112015000275 B1 | 2/2021 |
| CA | 2934499 C | 11/2020 |
| CN | 101156830 B | 5/2010 |
| CN | 101856389 A | 10/2010 |
| CN | 102293802 A | 12/2011 |
| CN | 102450972 A | 5/2012 |
| CN | 102613214 A | 8/2012 |
| CN | 102784079 A | 11/2012 |
| CN | 102940590 A | 2/2013 |
| CN | 103013307 A | 4/2013 |
| CN | 103387894 A | 11/2013 |
| CN | 103830226 A | 6/2014 |
| CN | 103845244 A | 6/2014 |
| CN | 103865692 A | 6/2014 |
| CN | 104013682 A | 9/2014 |
| CN | 104559580 A | 4/2015 |
| CN | 103341204 A | 8/2015 |
| CN | 105086747 A | 11/2015 |
| CN | 105199602 A | 12/2015 |
| CN | 103237538 B | 1/2016 |
| CN | 103788812 B | 4/2016 |
| CN | 104177970 B | 8/2016 |
| CN | 105816345 A | 8/2016 |
| CN | 105924604 A | 9/2016 |
| CN | 106147306 A | 11/2016 |
| CN | 106147539 A | 11/2016 |
| CN | 106413670 A | 2/2017 |
| CN | 106413674 A | 2/2017 |
| CN | 107158485 A | 9/2017 |
| CN | 107550826 A | 1/2018 |
| CN | 107652394 A | 2/2018 |
| CN | 108148474 A | 6/2018 |
| CN | 108610892 A | 10/2018 |
| CN | 108785119 A | 11/2018 |
| CN | 109010090 A | 12/2018 |
| CN | 109077946 A | 12/2018 |
| CN | 109321054 A | 2/2019 |
| CN | 109337508 A | 2/2019 |
| CN | 109350556 A | 2/2019 |
| CN | 109651907 A | 4/2019 |
| CN | 110003703 A | 7/2019 |
| CN | 110354296 A | 10/2019 |
| CN | 110381973 A | 10/2019 |
| CN | 110876715 A | 3/2020 |
| CN | 111032011 A | 4/2020 |
| CN | 111072098 A | 4/2020 |
| CN | 106572954 A | 6/2020 |
| CN | 108299667 A | 7/2020 |
| CN | 111593434 A | 8/2020 |
| CN | 108135876 B | 10/2020 |
| CN | 112386559 A | 2/2021 |
| EP | 1046390 A1 | 10/2000 |
| EP | 1543823 A1 | 6/2005 |
| EP | 1798279 A1 | 6/2007 |
| EP | 1633193 B1 | 5/2016 |
| EP | 1948124 B1 | 5/2016 |
| EP | 3120831 A1 | 1/2017 |
| EP | 3084066 B1 | 10/2017 |
| EP | 3243861 A1 | 11/2017 |
| EP | 3409112 A1 | 12/2018 |
| EP | 3261609 B1 | 4/2021 |
| GB | 1576136 A | 10/1980 |
| GB | 2097811 A | 11/1982 |
| GB | 2554000 A | 3/2018 |
| IL | 203403 | 11/2010 |
| JP | 63007785 A2 | 1/1988 |
| JP | 10218940 A2 | 8/1998 |
| JP | 2000044419 A | 2/2000 |
| JP | 2000110099 A2 | 4/2000 |

(56) References Cited

FOREIGN PATENT DOCUMENTS

| | | |
|---|---|---|
| JP | 3965006 B2 | 8/2007 |
| JP | 2019119725 A | 7/2019 |
| KR | 20110058754 A | 6/2011 |
| KR | 101376474 B1 | 3/2014 |
| KR | 101515865 B1 | 5/2015 |
| KR | 2017051006 A | 5/2017 |
| KR | 2059919 B1 | 12/2019 |
| KR | 2135648 B1 | 7/2020 |
| KR | 2021013582 A | 2/2021 |
| MX | 2014007137 A | 9/2014 |
| RU | 2452463 C1 | 6/2012 |
| RU | 2013131391 A | 1/2015 |
| RU | 2019110798 A | 11/2020 |
| WO | WO9400016 A1 | 1/1994 |
| WO | WO0128340 A2 | 4/2001 |
| WO | WO0132132 A2 | 5/2001 |
| WO | WO03006192 A1 | 8/2003 |
| WO | WO03092382 A1 | 11/2003 |
| WO | WO-2004010783 A1 * | 2/2004 ............ A01N 65/00 |
| WO | WO2004062703 A1 | 7/2004 |
| WO | WO2006085975 A2 | 8/2006 |
| WO | 08123115 A1 | 10/2008 |
| WO | 2009036030 A1 | 3/2009 |
| WO | WO2009065023 A1 | 5/2009 |
| WO | WO2010056685 A2 | 5/2010 |
| WO | 2011079163 A1 | 6/2011 |
| WO | WO2011083401 A2 | 7/2011 |
| WO | WO2013016029 A1 | 1/2013 |
| WO | WO2013052545 A1 | 4/2013 |
| WO | WO2013066403 A1 | 5/2013 |
| WO | 2013089720 A1 | 6/2013 |
| WO | WO2014032696 A1 | 3/2014 |
| WO | 2014098822 A1 | 6/2014 |
| WO | 2014098824 A1 | 6/2014 |
| WO | 2014098827 A1 | 6/2014 |
| WO | 2014098829 A1 | 6/2014 |
| WO | 14103475 A1 | 7/2014 |
| WO | WO2014113269 A1 | 7/2014 |
| WO | WO2014139904 A1 | 9/2014 |
| WO | 14163075 A1 | 10/2014 |
| WO | 2015014818 A2 | 2/2015 |
| WO | WO2015166075 A1 | 11/2015 |
| WO | WO2016018473 A1 | 2/2016 |
| WO | WO2016018474 A1 | 2/2016 |
| WO | WO2016018475 A1 | 2/2016 |
| WO | WO-2016018476 A1 * | 2/2016 ............ A61K 8/34 |
| WO | WO2016018476 A1 | 2/2016 |
| WO | 2016054021 A1 | 4/2016 |
| WO | 2016083798 A1 | 6/2016 |
| WO | 2016104602 A1 | 6/2016 |
| WO | 2016186896 A1 | 11/2016 |
| WO | 2017011665 A1 | 1/2017 |
| WO | 2017011679 A1 | 1/2017 |
| WO | 2017131691 A1 | 8/2017 |
| WO | 2019108218 A1 | 6/2019 |
| WO | 2019115806 A1 | 6/2019 |

OTHER PUBLICATIONS

Trimethylpentanediol-adipic acid-glycerin crosspolymer—Google search Sep. 13, 2019 (Year: 2019).*
Google search for "wet film by inolex" carried out Mar. 23, 2020 (Year: 2020).*
Google Scholar Search_Aug. 3, 2020_pyrogenic silica antimicrobial (Year: 2020).*
Google Scholar Search_Aug. 3, 2020_pyrogenic silica (Year: 2020).*
Co-pending U.S. Appl. No. 16/011,248, filed Jun. 18, 2018, by Chaudhary et al. for "Anti-Adherent Alcohol-Based Composition."
Co-pending U.S. Appl. No. 16/071,343, filed Jul. 19, 2018, by Engelbrecht et al. for "Adherent Composition for RNA Viruses and Method of Removing RNA Viruses from a Surface."
Co-pending U.S. Appl. No. 16/071,328, filed Jul. 19, 2018, by Engelbrecht et al. for "Anti-Adherent Composition Against DNA Viruses and Method of Inhibiting the Adherence of DNA Viruses to a Surface."
Katsikogianni, M. and Y.F. Missirlis, "Concise Review of Mechanisms of Bacterial Adhesion to Biomaterials and of Techniques Used in Estimating Bacteria-Material Interactions," European Cells and Materials, vol. 8, University of Patras, Patras, Greece, Dec. 2004, pp. 37-57.
Hwang et al (Resveratrol antibacterial activity against *Escherichia coli* is mediated by Z-ring formation inhibition via suppression of FtsZ expression. Scientific Reports vol. 5, Article No. 10029 (2015) (Year: 2015).
Al-Waili et al (Honey and microbial infections: a review supporting the use of honey for microbial control. J Med Food. Oct. 2011; 14 (10):1079-96) (Year: 2011).
"Soy Based Sauce", Mintel GNPD, https://www.gnpd.com/sinatra/recordpage/2694235/?utm_source=fed_search, Published Sep. 2014.
"Ginkgo Green Tea Drink", Mintel GNPD, https://www.gnpd.com/sinatra/recordpage/2683087/?utm_source=fed_search, Published Sep. 2014.
"June Premium Soy Sauce", Mintel GNPD, https://www.gnpd.com/sinatra/recordpage/2696123/?utm_source=fed_search, Published Sep. 2014.
Shan et al, "Antibacterial properties of Polygonum cuspidatum roots and their major bioactive consitiuents," Food Chemistry 109 (2008) 530-537.
Pitusiak, Ewelina, "Skin Care Formulations with Structure (RTM) Cell Thickeners", Nov. 18, 2011.
Al-Saedi, Fitua Minuar Aziz et al., "Development of a bacterial adhesin into a next generation antimicrobial agent" University of Birmingham, 2018, https://etheses.bham.ac.uk/id/eprint/8215/.
Jardak, Marwa et al., "Chemical composition, antibiofilm activities of Tunisian spices essential oils and combinatorial effect against *Staphylococcus epidermidis* biofilm", LWT, vol. 140, Apr. 2021, https://www.sciencedirect.com/science/article/abs/pii/S0023643820316790.
Kurniawan, Febrian Hendra et al., "Hydrophobic and antibacterial bed sheet using ZnO nanoparticles: A large-scale technique", Journal of Drug Delivery Science and Technology, vol. 62, Apr. 2021, https://www.sciencedirect.com/science/article/abs/pii/S1773224721000204.
Irwin, Nicola J. et al., "Infection-Triggered, Self-Cleaning Surfaces with On-Demand Cleavage of Surface-Localized Surfactant Moieties" ACS Biomater Sci Eng. Feb. 8, 2021, https://pubmed.ncbi.nlm.nih.gov/33502846/.
Sharifzadeh, Aghil et al., "Anti-adherence and anti-fungal abilities of thymol and carvacrol against candida species isolated from patients with oral candidiasis in comparison with fluconazole and voriconazole", Jundishapur Journal of Natural Pharmaceutical Products, Feb. 1, 2021.
Dera, Ayed A. et al., "Synergistic efficacies of thymoquinone and standard antibiotics against multi-drug resistant isolates", Saudi Med J., Feb. 2021, https://www.ncbi.nlm.nih.gov/pmc/articles/PMC7989283/.
Lencova, Simona et al., "Bacterial biofilms on polyamide nanofibers: Factors influencing biofilm formation and evaluation", ACS Publications, Dec. 7, 2020, https://pubs.acs.org/doi/pdf/10.1021/acsami.0c19016.
Rubini, Durairajan et al., "Chitosan coated catheters alleviates mixed species biofilms of *Staphylococcus epidermidis* and Candida albicans", Carbogydr Polym, Jan. 15, 2021, https://pubmed.ncbi.nlm.nih.gov/33183634/.
Habib, Salma et al., "Slippery liquid-infused porous polymeric surfaces based on natural oil with antimicrobial effect", Polymers, Jan. 2021, https://www.ncbi.nlm.nih.gov/pmc/articles/PMC7826890/pdf/polymers-13-00206.pdf.
Tektas, Sibel et al., "Initial bacterial adhesion and biofilm formation on aligner materials", Antibiotics, Dec. 15, 2020, https://www.ncbi.nim.nih.gov/pmclarticles/PMC7765154/pdf/antibiotics-09-00908.pdf.
Li, Xin et al., "Synthesis and Characterization of Hydrophobic Polystyrene Microspheres Film", Synthesis, Dec. 30, 2020, https://link.springer.com/article/10.1134/S1560090420060056.

(56) References Cited

OTHER PUBLICATIONS

Zheng, Kaiyuan et al., "Synergistic Antimicrobial Titanium Carbide (MXene) Conjugated with Gold Nanoclusters", Advanced Health Care Materials, Sep. 30, 2020, https://onlinelibrary.wiley.com/doi/abs/10.1002/adhm.202001007.

Sautrot-Ba, Pauline et al., "Photoinduced synthesis of antibacterial hydrogel from aqueous photoinitiating system", European Polymer Journal, vol. 138, Septembers, 2020, https://www.sciencedirect.com/science/article/abs/pii/s0014305720316505.

Singh, Amit Kumar et al., "Efficacy of Azadirachta indica essential oil bio-compounds against csuE among acinetobacter baumannii—An in-silico analysis", I.K. Press, vol. 21, Issue 33-34, Aug. 26, 2020, https://www.ikprress.org/index.php/PCBMB/article/view/5371.

Nelson, Jakline et al., "The biosurfactants iturin, lichenysin and surfactin, from vaginally isolated lactobacilli, prevent biofilm formation by pathogenic Candida", FEMS Microbiol Lett., Aug. 1, 2020, https://pubmed.ncbi.nlm.nih.gov/32710776/.

Rodrigues, Jeisa Zielle de Souza et al., "Antimicrobial activity of Lactobacillus fermentum TcUESCOI against *Streptococcus mutans* UA159", Microb Pathog, Feb. 24, 2020, https://pubmed.ncbi.nlm.nih.gov/32061821/.

Kokilakanit, P. et al., "A novel non-cytotoxic synthetic peptide, Pug-1, exhibited an antibiofilm effect on *Streptococcus mutans* adhesion", Lett Appl Microbiol, Mar. 2020, https://pubmed.ncbi.nlm.nih.gov/31837275/.

Modjinou, Tina et al., "Co-networks poly(Hydroxyalkanoates)-terpenes to enhance antibacterial properties", Bioengineering, Mar. 2020, https://www.ncbi.nlm.nih.gov/pmc/articles/PMC7148494/pdf/bioengineering-07-00013.pdf.

Boix-Lemonche, Gerard et al., "Covalent grafting of titanium with a cathelicidin peptide produces an osteoblast compatible surface with antistaphylococcal activity", Colloids and Surfaces B: Biointerfaces, vol. 185, Jan. 1, 2020, https://www.sciencedirect.com/science/article/abs/pii/S0927776519307301.

Arenas-Vivo, Ana et al., "An Ag-loaded photoactive nano-metal organic framework as a promising biofilm treatment", Acta Biomaterialia, vol. 97, Oct. 1, 2019, https://www.sciencedirect.com/science/article/abs/pii/S1742706119305586.

Cui, Xinnan et al., "Bacterial Inhibition and Osteoblast Adhesion on Ti Alloy Surfaces Modified by Poly(PEGMA-r-Phosmer) Coating", ACS Publications, Jun. 26, 2018, https://pubs.acs.org/doi/pdf/10.1021/acsami.8b07757.

Mortazavian, Hamid et al., "Understanding the role of shape and composition of star-shaped polymers and their ability to both bind and prevent bacteria attachment on oral relevant surfaces", J Funct Biomater, Dec. 17, 2019, https://www.ncbi.nlm.nih.gov/pmc/articles/PMC6963222/pdf/jfb-10-00056.pdf.

Marine, Jeannette et al., "Reduction of bacterial attachment on hydroxyapatite surfaces: Using hydrophobicity and chemical functionality to enhance surface retention and prevent attachment", Colloids Surf B Biointerfaces, Jul. 1, 2018, https://pubmed.ncbi.nlm.nih.gov/29730574/.

Mahyudin, Nor Ainy et al., "Bacterial attachment and biofilm formation on stainless steel surface and their in vitro inhibition by marine fungal extracts", Journal of Food Safety, Mar. 1, 2018, https://onlinelibrary.wiley.com/doi/abs/10.1111/jfs.12456.

Pathak, Rahul et al., "Inhibition of bacterial attachment and biofilm formation by a novel intravenous catheter material using an in vitro percutaneous catheter insertion model", Medical Devices: Evidence and Research, 2018, https://www.ncbi.nlm.nih.gov/pmc/articles/PMC6305250/pdf/mder-11-427.pdf.

Engelbrecht, Kathleen C. et al., "The effect of select personal care ingredients and simple formulations on the attachment of bacteria on polystyrene", Cosmetics, Jul. 10, 2018, https://www.google.com/url?sa=t&rcl-j&q-&esrc-s&source=web&cd-&ved-2ahUKEwjrzJiBrf3wAhU_wTgGHS30AH4QFjABegQIAhAD&url=https%3A%2F%2Fwww.mdpi.com%2F2079-9284%2F5%2F3%2F42%2Fpdf&usg=AOvVaw3ydupZOmoa9eFNSUaUskfW.

Wang, Yi et al., "Epigallocatechin gallate and gallic acid affect colonization of abiotic surfaces by oral bacteria", Arch Oral Biol., Dec. 2020, https://pubmed.ncbi.nlm.nih.gov/33045616/.

Sharifzadeh, Aghil et al., "Anti-adherence and Anti-fungal Abilities of Thymol and Carvacrol Against Candida Species Isolated From Patients with Oral Candidiasis in Comparison with Fluconazole and Voriconazole", Jundishapur Journal of Natural Pharmaceutical Products, Feb. 1, 2021, https://sites.kowsarpub.com/jjnpp/articles/65005.html.

Romera, D. et al., "Reduction Of Adherence Of Strictly Anaerobic Bacteria On Fluorine-Doped Titanium", Orthopaedic Proceedings, vol. 100-B, No. SUPP_3, Apr. 5, 2018, https://online.boneandjoint.org.uk/doi/abs/10.1302/1358-992X.2018.3.060.

He, Jiankang et al., "Nanocomplexes of carboxymethyl chitosan/amorphous calcium phosphate reduce oral bacteria adherence and biofilm formation on human enamel surface", J Dent. Jan. 2019, https://pubmed.ncbi.nlm.nih.gov/30423355/.

Kemung, Hefa Mangzira et al., "An Optimized Anti-adherence and Anti-biofilm Assay: Case Study of Zinc Oxide Nanoparticles versus MRSA Biofilm", Research Gate, Jun. 2020, https://www.researchgate.net/publication/342364559_An_Optimized_Anti-adherence_and_Anti-biofilm_Assay_Case_Study_of_Zinc_Oxide_Nanoparticles_versus_MRSA_Biofilm/link/5f2beb14299bf13404a61bda/download.

Simon, Gaelle et al., "Anti-biofilm and anti-adherence properties of novel cyclic dipeptides against oral pathogens", Bioorganic & Medicinal Chemistry, vol. 27, Issue 12, Jun. 2019, https://www.sciencedirect.com/science/article/abs/pii/S0968089618316547.

Abbas, Mohammed I. et al., "Surface Bacterial Adhesion Study of Novel Ternary PVC/ Polyester/ Bentonite Clay Nanocomposite Films", Current Physical Chemistry, vol. 11, Issue 1, 2021, https://www.eurekaselect.com/node/182844/article/surface-bacterial-adhesion-study-of-novel-ternary-pvc-polyester-bentonite-clay-nanocomposite-films.

Wang, Xiaodie et al., "Casein phosphopeptide combined with fluoride enhances the inhibitory effect on initial adhesion of *Streptococcus mutans* to the saliva-coated hydroxyapatite disc", BMC Oral Health, Article No. 169, 2020, https://bmcoralhealth.biomedcentral.com/articles/10.1186/s12903-020-01158-8.

Kerk, Swat Kim et al., "Bacteria Display Differential Growth and Adhesion Characteristics on Human Hair Shafts", Front Microbiol, 2018, https://www.ncbi.nlm.nih.gov/pmc/articles/PMC6137140/pdf/fmicb-09-02145.pdf.

Goc, Anna et al., "10-undecynoic acid is a new anti-adherent agent killing biofilm of oral *Streptococcus* spp." Plos One, Apr. 18, 2019, https://journals.plos.org/plosone/article?id=10.1371/journal.pone.0214763.

Prabha, Subramani et al., "Chitosan-Coated Surgical Sutures Prevent Adherence and Biofilms of Mixed Microbial Communities", Current Microbiology, 2021, https://link.springer.com/article/10.1007/s00284-020-02306-7.

\* cited by examiner

ANTI-ADHERENT COMPOSITIONS AND METHODS OF INHIBITING THE ADHERENCE OF MICROBES TO A SURFACE

TECHNICAL FIELD

Disclosed are compositions with anti-adherent properties and methods of inhibiting the adherence of microbes to a surface. More specifically, disclosed are compositions that include an anti-adherent agent that inhibits the adherence of microbes to a surface and methods of using such compositions. The microbes may be at least one of DNA viruses, RNA viruses, Gram negative bacteria, or Gram positive bacteria. The composition may be applied to or incorporated into articles such as wipes, or into ointments, lotions, creams, salves, aerosols, gels, suspensions, sprays, foams, washes, or the like.

BACKGROUND OF THE DISCLOSURE

Communicable human infections pass from person to person through various means such as food, aerosols, surfaces and hands. For example, in the United States, foodborne pathogens alone cause an estimated 76 million cases of illness, 325,000 hospitalizations and 5,000 deaths per year. This results in the spending or loss of several billion dollars due to absenteeism, cost of medication, and hospitalization.

Foodborne pathogens are typically a result of poor cleaning of hands and surfaces on which food is prepared. In fact, the kitchen is one of the most contaminated sites in the home. High fecal and coliform concentrations can be found in sponges, dishcloths, and the kitchen sink. Of course, there are other pathogens lurking elsewhere in the home, at the office, and in public places such as public bathrooms, restaurants, malls, theaters, health-care facilities, etc. Such pathogens include bacteria, protein, active enzymes, viruses, and many other microbes that can lead to health problems.

DNA viruses, including the adenovirus, are among these pathogens that can be spread and lead to health problems, such as the common cold, sore throats, pneumonia, and diarrhea. Other DNA viruses include herpes viruses, such as HSV-1, HSV-2, cytomegalovirus, and Epstein-Barr. Other DNA viruses can lead to diseases such as smallpox and chickenpox. RNA viruses, including influenza, noroviruses, rhinoviruses, polio virus, and enteroviruses, are also common causes of diseases in humans. These viruses can lead to symptoms of vomiting, diarrhea, body aches, and fevers, among others. DNA and RNA viruses, like other pathogens, can be commonly spread by shaking hands with infected people or touching a surface or object with such viruses on it.

Gram negative bacteria can include *Escherichia coli* (*E. coli*) and other Gram negative rods (e.g., *Entereobacteria, Salmonella choleraesuis, Klebsiella pneumoniae, Pseudomonas aeruginosa*); Gram negative curved rods (e.g., *Vibrio, Heliobacter, Campylobacter*, etc.); and Gram negative cocci (e.g., *Neisseria*). Gram negative bacteria can cause diarrhea, urinary tract infections, respiratory illnesses and pneumonia, and other illnesses. Gram positive bacteria can include *Staphylococcus aureus* (*S. aureus*). Other Gram positive bacteria include Gram positive rods (e.g., *Bacillus, Clostridium, Listeria*, etc.) and Gram positive cocci (e.g., *Staphylococcus, Streptococcus*, etc.). Gram positive bacteria can cause skin infections, pneumonia, and meningitis, among other illnesses. Gram negative and Gram positive bacteria can be commonly spread by shaking hands with infected people or by touching a surface or object with such bacteria on it.

There are products used today that are used to clean skin and hard surfaces where pathogens may be deposited, such as soaps, hand sanitizers, sprays and wipes. However, even the most diligent efforts to keep clean can be hindered by factors such as surface topography, the presence of hair, and the like. These factors can cause pathogens to better adhere to a surface. Other limiting factors include skin sensitivity due to the handling of cleaning products or the application thereof.

There remains a need for methods of reducing the adherence of microbes to a surface as well as compositions for accomplishing the same. The anti-adherent composition can be applied to surfaces or incorporated into articles, wherein the compositions inhibit the adherence of microbes. Desirably, the compositions are skin friendly, cost effective, and convenient to use.

SUMMARY OF THE DISCLOSURE

In one aspect of the disclosure, a method of inhibiting microbes from attaching to a surface can include providing an anti-adherent composition. The anti-adherent composition can include an anti-adherent agent configured to inhibit microbes from attaching to the surface. The anti-adherent agent can be selected from the group consisting of: Acrylates Copolymer, Trimethylpentanediol/Adipic Acid/Glycerin Crosspolymer, Trimethylpentanediol/Adipic Acid copolymer, Ethylhexyl Stearate, Ethylhexyl Salicylate, Acrylates/C12-22 Alkylmethacrylate Copolymer, Octocrylene, Ethylene Oxide/Propylene Oxide Block Copolymer, and Polyquaternium-101, and any combinations thereof. The method can further include applying the composition to the surface. The method can also include allowing at least some of the composition to remain on the surface such that the anti-adherent agent inhibits microbes from attaching to the surface.

In another aspect of the disclosure, an anti-adherent composition for preventing microbes from attaching to a surface can include an anti-adherent agent and a humectant. The anti-adherent agent can be selected from the group consisting of: Trimethylpentanediol/Adipic Acid/Glycerin Crosspolymer, Trimethylpentanediol/Adipic Acid copolymer, Ethylhexyl Stearate, and Acrylates/C12-22 Alkylmethacrylate Copolymer, and any combinations thereof.

In yet another aspect of the disclosure, an anti-adherent composition for preventing microbes from attaching to a surface can include an anti-adherent agent and a humectant. The anti-adherent agent can be selected from the group consisting of: Acrylates Copolymer, Trimethylpentanediol/Adipic Acid/Glycerin Crosspolymer, Trimethylpentanediol/Adipic Acid copolymer, Ethylhexyl Stearate, Ethylhexyl Salicylate, Acrylates/C12-22 Alkylmethacrylate Copolymer, and Polyquaternium-101, and any combinations thereof. The anti-adherent composition can be non-antimicrobial.

DETAILED DESCRIPTION OF THE DISLOSURE

The present disclosure is directed to a method of inhibiting the adherence of microbes to a surface and an anti-adherent composition containing an anti-adherent agent and a carrier that inhibits the adherence of microbes to a surface. The composition can be applied to a surface in the form of a liquid, gel, or foam; or incorporated into a wash. In addition, the composition can be applied to a surface with a vehicle such as a wipe.

The anti-adherent composition may be used on biotic surfaces such as skin or plants; or abiotic surfaces such as food prep surfaces; hospital and clinic surfaces; household surfaces; automotive, train, ship and aircraft surfaces; and the like; as long as the surface is compatible with the ingredients of the composition. Applying the anti-adherent composition to such surfaces can help prevent the amount or the likelihood that microbes will adhere to those surfaces, thus, lessening the likelihood of further transferring of the microbes.

Importantly, preferred embodiments of the anti-adherent composition of the present disclosure are not antimicrobial ("non-antimicrobial"). In other words, in preferred embodiments the anti-adherent composition does not include an effective amount of any antimicrobial agent(s). For purposes of this disclosure, an effective amount of an antimicrobial agent can be considered as such a concentration such that a kill of a desired microbe reaches the $IC_{50}$ (inhibitory concentration 50%) for that desired microbe with that antimicrobial agent. The $IC_{50}$ is defined as the amount of antimicrobial agent that is able to reduce the population of a selected microbe by 50% at a defined contact time and incubation temperature. In some embodiments, the anti-adherent composition can be free of antimicrobial agents. In these preferred embodiments in which the anti-adherent composition is non-antimicrobial, the anti-adherent composition seeks to prevent attachment of microbes to a surface, not eradicate or inactivate the microbes. This distinction can provide a benefit for the effectiveness for preventing the further spreading of microbes as concerns grow about the increasing microbial resistance to common antimicrobial treatments. However, in some alternative embodiments, as will be discussed further below, it is contemplated that the anti-adherent composition can include antimicrobial agents at an effective amount such that the anti-adherent composition is antimicrobial.

Anti-adherent Agents

Anti-adherent agents suitable for use in the composition can inhibit microbes from attaching to a surface. Suitable anti-adherent agents can include Acrylates Copolymer, Trimethylpentanediol/Adipic Acid/Glycerin Crosspolymer, Trimethylpentanediol/Adipic Acid Copolymer, Ethylhexyl Stearate, Ethylhexyl Salicylate, Acrylates/C12-22 Alkylmethacrylate Copolymer, Octocrylene, Ethylene Oxide/Propylene Oxide Block Copolymer, and Polyquaternium-101. The anti-adherent agents can be non-antimicrobial.

An exemplary Acrylates Copolymer can be Carbopol® Aqua SF-1 Polymer available from The Lubrizol Corporation. An exemplary Trimethylpentanediol/Adipic Acid/Glycerin Crosspolymer can be Lexorez® 200 available from Inolex. An exemplary Trimethylpentanediol/Adipic Acid Copolymer can be Lexorez® TL-8 available from Inolex. An exemplary Ethylhexyl Stearate can be Cetiol® 868 available from BASF Corporation. An exemplary Ethylhexyl Salicylate can be Escalol® 587 available from Ashland Inc. An exemplary Acrylates/C12-22 Alkylmethacrylate Copolymer can be Allianz OPT available from Ashland Inc. An exemplary Octocrylene can be Escalol® 597 available from Ashland Inc. An exemplary Ethylene Oxide/Propylene Oxide Block Copolymer can be Pluronic® 85 available from BASF Corporation. An exemplary Polyquaternium-101 can be Deposilk Q1 available from Air Products and Chemicals, Inc.

Some embodiments of the anti-adherent compositions of the present disclosure can be suitably made with an anti-adherent agent in an amount of from about 0.01% (by the total weight of the composition) to about 20% (by total weight of the composition), or preferably from about 0.05% (by total weight of the composition) to about 15% (by total weight of the composition), or more preferably from about 0.1% (by total weight of the composition) to about 10% (by total weight of the composition). In some preferred embodiments, the anti-adherent composition can include an anti-adherent agent in an amount from about 2.0% (by the total weight of the composition) to about 5.0% (by the total weight of the composition). However, it is contemplated that anti-adherent compositions of the present disclosure can be outside of these ranges. For example, in some embodiments, the anti-adherent composition can include an anti-adherent agent that provides 100% of the total weight of the anti-adherent composition.

Carriers

The anti-adherent compositions of the present disclosure may be formulated with one or more conventional and compatible carrier materials. The anti-adherent composition may take a variety of forms including, without limitation, aqueous solutions, gels, balms, lotions, suspensions, creams, milks, salves, ointments, sprays, emulsions, oils, resins, foams, solid sticks, aerosols, and the like. Liquid carrier materials suitable for use in the instant disclosure include those well-known for use in the cosmetic and medical arts as a basis for ointments, lotions, creams, salves, aerosols, gels, suspensions, sprays, foams, washes, and the like, and may be used in their established levels.

Non-limiting examples of suitable carrier materials include water, emollients, humectants, polyols, surfactants, esters, perflurocarbons, silicones, and other pharmaceutically acceptable carrier materials. In one embodiment, the carrier is volatile, allowing for immediate deposition of the anti-adherent ingredient to the desired surface while improving overall usage experience of the product by reducing drying time. Non-limiting examples of these volatile carriers include 5 cst Dimethicone, Cyclomethicone, Methyl Perfluoroisobutyl Ether, Methyl Perfluorobutyl Ether, Ethyl Perfluoroisobutyl Ether and Ethyl Perfluorobutyl Ether. Unlike conventional volatile carriers such as ethanol or isopropyl alcohol, these carriers have no antimicrobial effect.

In one embodiment, the anti-adherent compositions can optionally include one or more emollients, which typically act to soften, soothe, and otherwise lubricate and/or moisturize the skin. Suitable emollients that can be incorporated into the compositions include oils such as alkyl dimethicones, alkyl methicones, alkyldimethicone copolyols, phenyl silicones, alkyl trimethylsilanes, dimethicone, dimethicone crosspolymers, cyclomethicone, lanolin and its derivatives, fatty esters, glycerol esters and derivatives, propylene glycol esters and derivatives, alkoxylated carboxylic acids, alkoxylated alcohols, fatty alcohols, and combinations thereof.

Some embodiments of the anti-adherent compositions may include one or more emollients in an amount of from about 0.01% (by total weight of the composition) to about 20% (by total weight of the composition), or from about 0.05% (by total weight of the composition) to about 10% (by total weight of the composition), or from about 0.10% (by total weight of the composition) to about 5% (by total weight of the composition).

In another embodiment the anti-adherent compositions include one or more esters. The esters may be selected from cetyl palmitate, stearyl palmitate, cetyl stearate, isopropyl laurate, isopropyl myristate, isopropyl palmitate, and combinations thereof. The fatty alcohols include octyldodecanol, lauryl, myristyl, cetyl, stearyl, behenyl alcohol, and combinations thereof. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients. Other suitable ester compounds for use in the anti-adherent compositions or the present disclosure are listed in the *International Cosmetic Ingredient Dictionary and Handbook,* 11th Edition, CTFA, (January, 2006) ISBN-10: 1882621360, ISBN-13: 978-1882621361, and in the 2007 *Cosmetic Bench Reference*, Allured Pub. Corporation (Jul. 15, 2007) ISBN-10: 1932633278, ISBN-13: 978-1932633276, both of which are incorporated by reference herein to the extent they are consistent herewith.

Humectants that are suitable as carriers in the anti-adherent compositions of the present disclosure include, for example, glycerin, glycerin derivatives, hyaluronic acid, hyaluronic acid derivatives, betaine, betaine derivatives amino acids, amino acid derivatives, glycosaminoglycans, glycols, polyols, sugars, sugar alcohols, hydrogenated starch hydrolysates, hydroxy acids, hydroxy acid derivatives, salts of PCA and the like, and combinations thereof. Specific examples of suitable humectants include honey, sorbitol, hyaluronic acid, sodium hyaluronate, betaine, lactic acid, citric acid, sodium citrate, glycolic acid, sodium glycolate, sodium lactate, urea, propylene glycol, butylene glycol, pentylene glycol, ethoxydiglycol, methyl gluceth-10, methyl gluceth-20, polyethylene glycols (as listed in the *International Cosmetic Ingredient Dictionary and Handbook* such as PEG-2 through PEG 10), propanediol, xylitol, maltitol, or combinations thereof. Humectants are beneficial in that they prevent or reduce the chance that the anti-adherent film, formed after the anti-adherent agent is applied to a surface, will crack.

The anti-adherent compositions of the disclosure may include one or more humectants in an amount of about 0.01% (by total weight of the composition) to about 20% (by total weight of the composition), or about 0.05% (by total weight of the composition) to about 10% by total weight of the composition), or about 0.1% (by total weight of the composition) to about 5.0% (by total weight of the composition).

The anti-adherent compositions may include water. For instance, where the anti-adherent composition is a wetting composition, such as described below for use with a wet wipe, the composition will typically include water. The anti-adherent compositions can suitably comprise water in an amount of from about 0.01% (by total weight of the composition) to about 99.98% (by total weight of the composition), or from about 1.00% (by total weight of the composition) to about 99.98% (by total weight of the composition), or from about 50.00% (by total weight of the composition) to about 99.98% (by total weight of the composition), or from about 75.00% (by total weight of the composition) to about 99.98% (by total weight of the composition).

In an embodiment where the anti-adherent composition serves as a wash (e.g. shampoo; surface cleaner; or hand, face, or body wash), the anti-adherent composition will include one or more surfactants. These may be selected from anionic, cationic, nonionic, zwitterionic, and amphoteric surfactants. Amounts may range from 0.1 to 30%, or from 1 to 20%, or from 3 to 15% by total weight of the composition.

Suitable anionic surfactants include, but are not limited to, $C_8$ to $C_{22}$ alkane sulfates, ether sulfates and sulfonates. Among the suitable sulfonates are primary $C_8$ to $C_{22}$ alkane sulfonate, primary $C_8$ to $C_{22}$ alkane disulfonate, $C_8$ to $C_{22}$ alkene sulfonate, $C_8$ to $C_{22}$ hydroxyalkane sulfonate or alkyl glyceryl ether sulfonate. Specific examples of anionic surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, potassium lauryl sulfate, sodium trideceth sulfate, sodium methyl lauroyl taurate, sodium lauroyl isethionate, sodium laureth sulfosuccinate, sodium lauroyl sulfosuccinate, sodium tridecyl benzene sulfonate, sodium dodecyl benzene sulfonate, sodium lauryl amphoacetate and mixtures thereof. Other anionic surfactants include the $C_8$ to $C_{22}$ acyl glycinate salts. Suitable glycinate salts include sodium cocoylglycinate, potassium cocoylglycinate, sodium lauroylglycinate, potassium lauroylglycinate, sodium myristoylglycinate, potassium myristoylglycinate, sodium palmitoylglycinate, potassium palmitoylglycinate, sodium stearoylglycinate, potassium stearoylglycinate, ammonium cocoylglycinate and mixtures thereof. Cationic counter-ions to form the salt of the glycinate may be selected from sodium, potassium, ammonium, alkanolammonium and mixtures of these cations.

Suitable cationic surfactants include, but are not limited to alkyl dimethylamines, alkyl amidopropylamines, alkyl imidazoline derivatives, quaternised amine ethoxylates, and quaternary ammonium compounds.

Suitable nonionic surfactants include, but are not limited to, alcohols, acids, amides or alkyl phenols reacted with alkylene oxides, especially ethylene oxide either alone or with propylene oxide. Specific nonionics are $C_6$ to $C_{22}$ alkyl phenols-ethylene oxide condensates, the condensation products of $C_8$ to $C_{13}$ aliphatic primary or secondary linear or branched alcohols with ethylene oxide, and products made by condensation of ethylene oxide with the reaction products of propylene oxide and ethylenediamine. Other nonionics include long chain tertiary amine oxides, long chain tertiary phosphine oxides and dialkyl sulphoxides, alkyl polysaccharides, amine oxides, block copolymers, castor oil ethoxylates, ceto-oleyl alcohol ethoxylates, ceto-stearyl alcohol ethoxylates, decyl alcohol ethoxylates, dinonyl phenol ethoxylates, dodecyl phenol ethoxylates, end-capped ethoxylates, ether amine derivatives, ethoxylated alkanolamides, ethylene glycol esters, fatty acid alkanolamides, fatty alcohol alkoxylates, lauryl alcohol ethoxylates, mono-branched alcohol ethoxylates, natural alcohol ethoxylates, nonyl phenol ethoxylates, octyl phenol ethoxylates, oleyl amine ethoxylates, random copolymer alkoxylates, sorbitan ester ethoxylates, stearic acid ethoxylates, stearyl amine ethoxylates, synthetic alcohol ethoxylates, tall oil fatty acid ethoxylates, tallow amine ethoxylates and trid tridecanol ethoxylates.

Suitable zwitterionic surfactants include, for example, alkyl amine oxides, silicone amine oxides, and combinations thereof. Specific examples of suitable zwitterionic surfactants include, for example, 4-[N,N-di(2-hydroxyethyl)-N- octadecylammonio]-butane-1-carboxylate, S-[S-3-hydroxypropyl-S-hexadecylsulfonio]-3-hydroxypentane-1-sulfate, 3-[P, P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-dodeoxy-2-hydroxypropyl(sulfonio]-propane-1-phosphonate, 3-[P, P-dimethyl-P-dodecylphosphonio]-propane-1-phosphonate, 5-[N,N-di(3-hydroxypropyl)-N-hexadecylammonio]-2-hydroxy-pentane-1-sulfate, and combinations thereof.

Suitable amphoteric surfactants include, but are not limited to, derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Illustrative amnphoterics are coco dimethyl carboxymethyl betaine, cocoamidopropyl betaine, cocobetaine, oleyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, cocoamphoacetates, and combinations thereof. The sulfobetaines may include stearyl dimethyl sulfopropyl betaine, lauryl dimethyl sulfoethyl betaine, lauryl bis-(2-hydroxyethyl) sulfopropyl betaine and combinations thereof.

Rheology Modifier

Optionally, one or more rheology modifiers, such as thickeners, may be added to the anti-adherent compositions. Suitable rheology modifiers are compatible with the anti-adherent agent. As used herein, "compatible" refers to a compound that, when mixed with the anti-adherent agent, does not adversely affect the anti-adherent properties of same.

A thickening system is used in the anti-adherent compositions to adjust the viscosity and stability of the compositions. Specifically, thickening systems prevent the composition from running off of the hands or body during dispensing and use of the composition. When the anti-adherent composition is used with a wipe product, a thicker formulation can be used to prevent the composition from migrating from the wipe substrate.

The thickening system should be compatible with the compounds used in the present disclosure; that is, the thickening system, when used in combination with the anti-adherent compounds, should not precipitate out, form a coacervate, or prevent a user from perceiving the conditioning benefit (or other desired benefit) to be gained from the composition. The thickening system may include a thickener which can provide both the thickening effect desired from the thickening system and a conditioning effect to the user's skin.

Thickeners may include, cellulosics, gums, acrylates, starches and various polymers. Suitable examples include are not limited to hydroxethyl cellulose, xanthan gum, guar gum, potato starch, and corn starch. In some embodiments, PEG-150 stearate, PEG-150 distearate, PEG-175 diisostearate, polyglyceryl-10 behenate/eicosadioate, disteareth-100 IPDI, polyacrylamidomethylpropane sulfonic acid, butylated PVP, and combinations thereof may be suitable.

While the viscosity of the compositions will typically depend on the thickener used and the other components of the compositions, the thickeners of the compositions suitably provide for a composition having a viscosity in the range of greater than 10 cP to about 30,000 cP or more. In another embodiment, the thickeners provide compositions having a viscosity of from about 100 cP to about 20,000 cP. In yet another embodiment, thickeners provide compositions having a viscosity of from about 200 cP to about 15,000 cP.

Typically, the anti-adherent compositions of the present disclosure include the thickening system in an amount of no more than about 20% (by total weight of the composition), or from about 0.01% (by total weight of the composition) to about 20% (by total weight of the composition). In another aspect the thickening system is present in the anti-adherent composition in an amount of from about 0.10% (by total weight of the composition) to about 10% (by total weight of the composition), or from about 0.25% (by total weight of the composition) to about 5% (by total weight of the composition), or from about 0.5% (by total weight of the composition) to about 2% (by total weight of the composition).

Foaming Agents

In one embodiment, the anti-adherent compositions can be delivered as a foam. In accordance with the present disclosure, in order to make the composition foamable, the composition is combined with a foaming agent such as at least one derivatized dimethicone.

The foaming agent is capable of causing the compositions to foam when the compositions are combined with air using, for instance, a manual pump dispenser. Although the anti-adherent compositions may be dispensed from an aerosol container, an aerosol is not needed in order to cause the compositions to foam. Also of particular advantage, the compositions are foamable without having to include fluorinated surfactants.

Various different derivatized dimethicone foaming agents may be used in the compositions of the present disclosure. The derivatized dimethicone, for instance, may comprise a dimethicone copolyol, such as an ethoxylated dimethicone. In one embodiment, the derivatized dimethicone is linear, although branched dimethicones may be used.

The amount of foaming agent present in the foaming compositions can depend upon various factors and the desired result. In general, the foaming agent can be present in an amount from about 0.01% to about 10% (by total weight of the composition), or from about 0.1% to about 5% (by total weight of the composition), or from about 0.1% to about 2% (by total weight of the composition).

When an anti-adherent composition is made foamable, it may be contained in an aerosol container. In an aerosol container, the composition is maintained under pressure sufficient to cause foam formation when dispensed.

Emulsifiers

In one embodiment, the anti-adherent compositions may include hydrophobic and hydrophilic ingredients, such as a lotion or cream. Generally, these emulsions have a dispersed phase and a continuous phase, and are generally formed with the addition of a surfactant or a combination of surfactants with varying hydrophilic/lipopiliclipophilic balances (HLB). Suitable emulsifiers include surfactants having HLB values from 0 to 20, or from 2 to 18. Suitable non-limiting examples include Ceteareth-20, Cetearyl Glucoside, Ceteth-10, Ceteth-2, Ceteth-20, Cocamide MEA, Glyceryl Laurate, Glyceryl Stearate, PEG-100 Stearate, Glyceryl Stearate, Glyceryl Stearate SE, Glycol Distearate, Glycol Stearate, Isosteareth-20, Laureth-23, Laureth-4, Lecithinm, Methyl Glucose Sesquistearate, Oleth-10, Oleth-2, Oleth-20, PEG-100 Stearate, PEG-20 Almond Glycerides, PEG-20 Methyl Glucose Sesquistearate, PEG-25 Hydrogenated Castor Oil, PEG-30 Dipolyhydroxystearate, PEG-4 Dilaurate, PEG-40 Sorbitan Peroleate, PEG-60 Almond Glycerides, PEG-7 Olivate, PEG-7 Glyceryl Cocoate, PEG-8 Dioleate, PEG-8 Laurate, PEG-8 Oleate, PEG-80 Sorbitan Laurate, Polysorbate 20, Polysorbate 60, Polysorbate 80, Polysorbate 85, Propylene Glycol Isostearate, Sorbitan Isostearate, Sorbitan Laurate, Sorbitan Monostearate, Sorbitan Oleate, Sorbitan Sesquioleate, Sorbitan Stearate, Sorbitan Trioleate, Stearamide MEA, Steareth-100, Steareth-2, Steareth-20, Steareth-21. The compositions can further include surfactants or combinations of surfactants that create liquid crystalline networks or liposomal networks. Suitable non-limiting examples include OLIVEM 1000 (INCI: Cetearyl Olivate (and) Sorbitan Olivate (available from HallStar Company (Chicago, Ill.)); ARLACEL LC (INCI: Sorbitan Stearate (and) Sorbityl Laurate, commercially available from Croda (Edison, NJ)); CRYSTALCAST MM (INCI: Beta Sitosterol (and) Sucrose Stearate (and) Sucrose Distearate (and) Cetyl Alcohol (and) Stearyl Alcohol, commercially available from MMP Inc. (South Plainfield, NJ)); UNIOX CRISTAL (INCI: Cetearyl Alcohol (and) Polysorbate 60 (and) Cetearyl Glucoside, commercially available from Chemyunion (Sao Paulo, Brazil)). Other suitable emulsifiers include lecithin, hydrogenated lecithin, lysolecithin, phosphatidylcholine, phospholipids, and combinations thereof.

Adjunct Ingredients

The anti-adherent compositions of the present disclosure may additionally include adjunct ingredients conventionally found in pharmaceutical compositions in an established fashion and at established levels. For example, the anti-adherent compositions may comprise additional compatible pharmaceutically active and compatible materials for combination therapy, such as antioxidants, anti-parasitic agents, antipruritics, antifungals, antiseptic actives, biological actives, astringents, keratolytic actives, local anaesthetics, anti-stinging agents, anti-reddening agents, skin soothing agents, external analgesics, film formers, skin exfoliating agents, sunscreens, and combinations thereof.

Other suitable additives that may be included in the anti-adherent compositions of the present disclosure include compatible colorants, deodorants, emulsifiers, anti-foaming agents (when foam is not desired), lubricants, skin conditioning agents, skin protectants and skin benefit agents (e.g., aloe vera and tocopheryl acetate), solvents, solubilizing agents, suspending agents, wetting agents, pH adjusting ingredients (a suitable pH range of the compositions can be from about 3.5 to about 8), chelators, propellants, dyes and/or pigments, and combinations thereof.

Another component that may be suitable for addition to the anti-adherent compositions is a fragrance. Any compatible fragrance may be used. Typically, the fragrance is present in an amount from about 0% (by weight of the composition) to about 5% (by weight of the composition), and more typically from about 0.01% (by weight of the composition) to about 3% (by weight of the composition). In one desirable embodiment, the fragrance will have a clean, fresh and/or neutral scent to create an appealing delivery vehicle for the end consumer.

Organic sunscreens that may be present in the anti-adherent compositions include ethylhexyl methoxycinnamate, avobenzone, octocrylene, benzophenone-4, phenyl-benzimidazole sulfonic acid, homosalate, oxybenzone, benzophenone-3, ethylhexyl salicylate, and mixtures thereof.

As previously noted, in some embodiments, antimicrobial agents can be added to the anti-adherent compositions as optional ingredients. For example, suitable antimicrobials include biocides such as a short-chain alcohol, benzoalkonium chloride ("BAC"), didecyl dimethyl ammonium chloride ("DDAC"), and zeolite ("CWT-A"). Other possible antimicrobial agents include: isothiazolone, alkyl dimethyl ammonium chloride, a triazine, 2-thiocyanomethylthio benzothiazol, methylene bis thiocyanate, acrolein, dodecylguanidine hydrochloride, a chlorophenol, a quaternary ammonium salt, gluteraldehyde, a dithiocarbamate, 2-mercatobenzothiazole, para-chloro-meta-xylenol, silver, chlorohexidine, polyhexamthylene biguanide, a n-halamine, triclosan, a phospholipid, an alpha hydroxyl acid, 2,2-dibromo-3-nitrilopropionamide, 2-bromo-2-nitro-1,3-propanediol, farnesol, iodine, bromine, hydrogen peroxide, chlorine dioxide, a botanical oil, a botanical extract, benzalkonium chloride, chlorine, sodium hypochlorite, or combinations thereof. In some embodiments, the antimicrobial agent can be antibacterial. In some embodiments, the antimicrobial agent can be antiviral. In some embodiments, the antimicrobial agent can be antibacterial and antiviral.

If present, the amount of the antimicrobial agent in the anti-adherent compositions can be in an amount between about 0.01% to about 5% (by total weight of the composition), or in some embodiments between about 0.05% to about 3% (by total weight of the composition). In some embodiments, the antimicrobial agent can be provided to the anti-adherent composition at an effective amount such that a kill of a desired microbe reaches the $IC_{50}$ (inhibitory concentration 50%) for that desired microbe with that antimicrobial agent in the anti-adherent composition. In some embodiments, the antimicrobial agent can be provided to the anti-adherent composition at less than an effective amount such that a kill of a desired microbe does not reach the $IC_{50}$ for that desired microbe with that antimicrobial agent in the anti-adherent composition, in which case the anti-adherent composition would still be considered non-antimicrobial for purposes of this disclosure. As previously noted, antimicrobial agents are merely optional ingredients.

Preservatives

The anti-adherent compositions may include various preservatives to increase shelf life. Some suitable preservatives that may be used in the present disclosure include, but are not limited to phenoxyethanol, capryl glycol, glyceryl caprylate, sorbic acid, gallic acid, KATHON CG®, which is a mixture of methylchloroisothiazolinone and methylisothiazolinone, (available from Rohm & Haas Company, Philadelphia, Pa.); DMDM hydantoin (e.g., GLYDANT, available from Lonza, Inc., Fair Lawn, N.J.); EDTA and salts thereof; iodopropynyl butylcarbamate; benzoic esters (parabens), such as methylparaben, propylparaben, butylparaben, ethylparaben, isopropylparaben, isobutylparaben, benzylparaben, sodium methylparaben, and sodium propylparaben; 2-bromo-2-nitropropane-1,3-diol; benzoic acid; and the like. Other suitable preservatives include those sold by Sutton Labs Inc., Chatham, N.J., such as "GERMALL 115" (imidazolidinyl urea), "GERMALL II" (diazolidinyl urea), and "GERMALL PLUS" (diazolidinyl urea and iodopropynyl butylcarbonate).

The amount of the preservative in the anti-adherent compositions is dependent on the relative amounts of other components present within the composition. For example, in some embodiments, the preservative is present in the compositions in an amount between about 0.001% to about 5% (by total weight of the composition), in some embodiments between about 0.01 to about 3% (by total weight of the composition), and in some embodiments, between about 0.05% to about 1.0% (by total weight of the composition).

Preparation of Anti-adherent Compositions

The anti-adherent compositions of the present disclosure may be prepared by combining ingredients at room temperature and mixing.

In one embodiment, when the anti-adherent composition is to be applied to the skin of an individual, the composition includes the anti-adherent agent, a hydrophilic carrier and a hydrophilic thickener. Suitable hydrophilic carriers can be, for example, water, glycerin, glycerin derivatives, glycols, water-soluble emollients, and combinations thereof. Suitable examples of glycerin derivatives could include, but are not to be limited to, PEG-7 glyceryl cocoate. Suitable glycols could include, but are not to be limited to, propylene glycol, butylene glycol, pentylene glycol, ethoxydiglycol, dipropylene glycol, propanediol, and PEG-8. Suitable examples of water-soluble emollients could include, but are not to be limited to, PEG-6 Caprylic Capric Glycerides, Hydrolyzed Jojoba Esters, and PEG-10 Sunflower Glycerides.

Delivery Vehicles

The anti-adherent compositions of the present disclosure may be used in combination with a product. For example, the composition may be incorporated into or onto a substrate, such as a wipe substrate, an absorbent substrate, a fabric or cloth substrate, a tissue or paper towel substrate, or the like. In one embodiment, the anti-adherent composition may be used in combination with a wipe substrate to form a wet wipe or may be a wetting composition for use in combination with a wipe which may be dispersible. In other embodiments, the anti-adherent composition may be incorporated into wipes such as wet wipes, hand wipes, face wipes, cosmetic wipes, cloths and the like. In yet other embodiments, the anti-adherent compositions described herein can be used in combination with numerous personal care products, such as absorbent articles. Absorbent articles of interest are diapers, training pants, adult incontinence products, feminine hygiene products, and the like; bath or facial tissue; and paper towels. Personal protective equipment articles of interest include but are not limited to masks, gowns, gloves, caps, and the like.

In one embodiment, the wet wipe may comprise a nonwoven material that is wetted with an-aqueous solution termed the "wetting composition," which may include or be composed entirely of the anti adherent compositions disclosed herein. As used herein, the nonwoven material comprises a fibrous material or substrate, where the fibrous material or substrate comprises a sheet that has a structure of individual fibers or filaments randomly arranged in a mat-like fashion. Nonwoven materials may be made from a variety of processes including, but not limited to, airlaid processes, wet-laid processes such as with cellulosic-based tissues or towels, hydroentangling processes, staple fiber carding and bonding, melt blown, and solution spinning.

The fibers forming the fibrous material may be made from a variety of materials including natural fibers, synthetic fibers, and combinations thereof. The choice of fibers may depend upon, for example, the intended end use of the finished substrate and the fiber cost. For instance, suitable fibers may include, but are not limited to, natural fibers such as cotton, linen, jute, hemp, wool, wood pulp, etc. Similarly, suitable fibers may also include: regenerated cellulosic fibers, such as viscose rayon and cuprammonium rayon; modified cellulosic fibers, such as cellulose acetate; or synthetic fibers, such as those derived from polypropylenes, polyethylenes, polyolefins, polyesters, polyamides, polyacrylics, etc. Regenerated cellulose fibers, as briefly discussed above, include rayon in all its varieties as well as other fibers derived from viscose or chemically modified cellulose, including regenerated cellulose and solvent-spun cellulose, such as Lyocell. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Chemically treated natural cellulosic fibers may be used, such as mercerized pulps, chemically stiffened or crosslinked fibers, or sulfonated fibers.

In addition, cellulose produced by microbes and other cellulosic derivatives may be used. As used herein, the term "cellulosic" is meant to include any material having cellulose as a major constituent, and, specifically, comprising at least 50 percent by weight cellulose or a cellulose derivative. Thus, the term includes cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose. Blends of one or more of any of the previously described fibers may also be used, if so desired.

The fibrous material may be formed from a single layer or multiple layers. In the case of multiple layers, the layers are generally positioned in a juxtaposed or surface-to-surface relationship and all or a portion of the layers may be bound to adjacent layers. The fibrous material may also be formed from a plurality of separate fibrous materials wherein each of the separate fibrous materials may be formed from a different type of fiber.

Airlaid nonwoven fabrics are particularly well suited for use as wet wipes. The basis weights for airlaid nonwoven fabrics may range from about 20 to about 200 grams per square meter (gsm) with staple fibers having a denier of about 0.5 to about 10 and a length of about 6 to about 15 millimeters. Wet wipes may generally have a fiber density of about 0.025 g/cc to about 0.2 g/cc. Wet wipes may generally have a basis weight of about 20 gsm to about 150 gsm. More desirably the basis weight may be from about 30 to about 90 gsm. Even more desirably the basis weight may be from about 50 gsm to about 75 gsm.

Processes for producing airlaid non-woven basesheets are described in, for example, published U.S. Pat. App. No. 2006/0008621, herein incorporated by reference to the extent it is consistent herewith.

As a result of the present disclosure, it has been discovered that an anti-adherent composition including an anti-adherent agent can be employed to inhibit the adherence of microbes to a surface. Thus, in one embodiment, an anti-adherent composition can be applied to a surface (e.g., countertop, wall, table, skin, etc.). At least some of the anti-adherent composition can be allowed to remain on the surface such that the anti-adherent agent can inhibit microbes from attaching to the surface, and therefore, reduce the amount of microbes that will adhere to that surface. By reducing the amount of microbes that will adhere to that surface, the anti-adherent composition can be used to reduce the likelihood that individuals come into contact with microbes, and thereby reduce the spreading of the microbes. This benefit could be provided whether the anti-adherent composition was provided in the form of a liquid, gel, or foam; or incorporated into a wash, or is provided on or in a delivery vehicle such as a fibrous substrate (e.g., a wipe).

The disclosure will be more fully understood upon consideration of the following non-limiting examples described in the following section on testing.

TESTING

From testing conducted and as described further below, it has been discovered that an anti-adherent composition including an anti-adherent agent of the present disclosure can inhibit microbes from attaching or adhering to a surface. The anti-adherent agent can be selected from the group consisting of: Acrylates Copolymer, Trimethylpentanediol/Adipic Acid/Glycerin crosspolymer, Trimethylpentanediol/Adipic Acid Copolymer, Ethylhexyl Stearate, Ethylhexyl Salicylate, Acrylates/C12-22 Alkylmethacrylate Copolymer, Octocrylene, Ethylene Oxide/Propylene Oxide Block Copolymer, and Polyquaternium-101, and any combinations thereof. Anti-adherent compositions including the anti-adherent agents of Acrylates Copolymer and Ethylhexyl Stearate provided an anti-adherent effect against each of the types of microbes Gram Negative bacteria, Gram positive bacteria, DNA viruses, and RNA viruses in the testing conducted and as described further below. Anti-adherent compositions including other anti-adherent agents provided an anti-adherent effect against one or more, but not all, of the types of microbes tested.

Attachment Against Bacteria

Anti-adherent compositions including anti-adherent agents as discussed herein were tested against bacteria using the High Throughput Attachment Test Method. The High Throughput Attachment Test Method is discussed in further detail below. The anti-adherent compositions including the anti-adherent agents were tested against Gram-positive Staphylococcus aureus, and Gram-negative Escherichia coli. The pH of the compositions for this testing between 3 to 10 pH, or about 4 to about 8 pH. The results of the testing is shown below in Table 1.

TABLE 1

Compounds and corresponding ratio of bacteria growth on treated pegs to untreated pegs according to High Throughput Attachment Test Method

| # | Compound Type | Compound Name (Manufacturer) | Con. Wt. %* | INCI Name | Ratio of E. coli growth on treated pegs to untreated pegs (%) | Ratio of S. aureus growth on treated pegs to untreated pegs (%) |
|---|---|---|---|---|---|---|
| 1 | Synthetc Polymer | Deposilk Q1 (Air Products and Chemicals, Inc.) | 5 | Polyquaternium-101 | 87.8 | 104.9 |
| 2 | Synthetic Polymer | Allianz OPT (Ashland Inc.) | 2 | Acrylates/C12-22 Alkylmethacrylate Copolymer | 89.7 | 73.4 |
| 3 | Synthetic Polymer | Carbopol ® Aqua SF-1 (Lubrizol Corporation) | 2 | Acrylates Copolymer | 71.5 | 55.6 |
| 4 | Synthetic Polymer | Lexorez ® 200 (Inolex) | 5 | Trimethylpentanediol/ Adipic Acid/Glycerin Crosspolymer | 92.8 | 99.4 |
| 5 | Synthetic Polymer | Lexorez ® TL-8 (Inolex) | 5 | Trimethylpentanediol/ Adipic Acid Copolymer | 82.5 | 96.4 |
| 6 | Synthetic Polymer | Pluronic ® 85 (BASF Corporation) | 5 | Ethylene Oxide/Propylene Oxide Block Copolymer | 113.7 | 55.8 |
| 7 | Cosmetic Oil (Ester) | Cetiol ® 868 (BASF Corporation) | 100 | Ethylhexyl Stearate | 48.4 | 68.6 |
| 8 | Cosmetic Oil (Ester) | Escalo ®l 587 (Ashland Inc.) | 100 | Ethylhexyl Salicylate | 111.1 | 75.4 |
| 9 | Cosmetic Oil (Ester) | Escalol ® 597 (Ashland Inc.) | 100 | Octocrylene | 114.1 | 81.9 |

*Con. Wt. % = Concentration of Compound in 5% glycerin and QS water, by total weight of solution, unless compound was tested at 100% concentration As shown in the results of Table 1 above and based on the categorization as described by the High Throughput Attachment Test Method (a ratio of bacterial growth on treated pegs to untreated pegs less than 85% being anti-adherent at a statistically significant level), the anti-adherent compositions including the anti-adherent agents of Acrylates Copolymer and Ethylhexyl Stearate provided an anti-adherent effect against both Gram negative bacteria (*E. coli*) and Gram positive bacteria (*S. aureus*). The anti-adherent composition including the anti-adherent agent of Trimethylpentanediol/Adipic Acid Copolymer provided an anti-adherent effect against Gram negative bacteria (*E. coli*), but was neutral-adherent agents of Acrylates/C12-22 Alkylmethacrylate Copolymer, Ethylene Oxide/Propylene Oxide Block Copolymer, Ethylhexyl Salicylate, and Octocrylene provided an anti-adherent effect against Gram positive bacteria (*S. aureus*), but was neutral against Gram negative bacteria (*E. coli*).

Attachment Against RNA and DNA Viruses

The anti-adherent compositions that inhibit the attachment of RNA and/or DNA viruses to a surface including compounds serving as anti-adherent agents against RNA and DNA viruses were tested against RNA and DNA viruses via the High Throughput Test to Quantify the Attachment of Phage to a Surface, as discussed in detail below. Tables 2 and 3 below show the variety of compounds that were tested as agents in a composition, as well as the results that related to the percent reduction in viruses and the Logarithmic Reduction compared to growth controls. As will be discussed in further detail below in the discussion regarding the High Throughput Test to Quantify the Attachment of Phage to a Surface, a positive logarithmic reduction in viruses equates to anti-adherent properties (e.g., inhibits attachment), and a negative logarithmic reduction in viruses equates to adherent properties (e.g., increases attachment).

The RNA virus that the compositions were tested against for attachment behaviors was MS2. Bacteriophage are commonly utilized as surrogates of mammalian viruses in both medical and virology applications. MS2 phage is commonly utilized as a viral surrogate because of its size, morphology, environmental stability, non-human infectivity, and the ability for use in high throughput assays. Additionally, MS2 is commonly used as a surrogate to study the spread of human Norovirus (See, Tung-Thompson, et al, *PLoS One*, 2015, 10(8): e0134277, Dawson D J, et al, *J App Micro*, 2005, 98: 203-209, Jones, et al, *J Hosp Infect*, 1991, 17:279-85). The use of MS2 phage in hand sanitizer studies makes it an ideal surrogate to study the interaction of personal care products and viral attachment. It is believed that compositions including the adherent agents noted above would act in a substantially similar behavior to other RNA viruses as they did against MS2.

The DNA virus that the compositions were tested against for attachment behaviors was Phi X 174. Bacteriophage are commonly utilized as surrogates of mammalian viruses in both medical and virology applications. Phi X 174 is commonly utilized as a viral surrogate because of its size, morphology, environmental stability, and non-human infectivity, and the ability for use in high throughput assays. Phi X174 has been previously been used to study barrier efficacy, making it an ideal surrogate to study attachment to a surface (See, Haman and Nelson, *Am J Infect Control*, 1993, 21:289-96, O'Connell, et al, *Clin Microb Infect*, 2004, 10:322-6, ASTM F1671/F1671M-13, Standard Test Method for Resistance of Materials Used in Protective Clothing to Penetration by Blood-Borne Pathogens Using Phi X174 Bacteriophage Penetration as a Test System). Thus, it is well accepted by those of ordinary skill in the art that Phi X 174 serves as a surrogate for other DNA viruses, and the compositions including the adherent agents noted above would act in a substantially similar behavior to other DNA viruses as they did against Phi X 174.

As can be seen from Table 2, several of the compounds exhibited positive logarithmic reductions in testing against RNA viruses at statistically significant levels, and thus, can help to inhibit adherence of an RNA virus to a surface. Additionally, as can be seen from Table 3 below, several of the compounds exhibited positive logarithmic reductions in testing against DNA viruses at statistically significant levels, and thus, can help to inhibit adherence of a DNA virus to a surface. The anti-adherent compositions including the anti-adherent agents of Acrylates Copolymer, Trimethylpentanediol/Adipic Acid/Glycerin Crosspolymer, Trimethylpentanediol/Adipic Acid Copolymer, Ethylhexyl Stearate, and Ethylhexyl Salicylate provided an anti-adherent effect against both RNA viruses and DNA viruses. The anti-adherent compositions including the anti-adherent agent of Polyquaternium-101 provided an anti-adherent effect against RNA viruses, but was neutral against DNA viruses. The anti-adherent compositions including the anti-adherent agents of Acrylates/C12-22 Alkylmethacrylate Copolymer, Ethylene Oxide/Propylene Oxide Block Copolymer, and Octocrylene provided an anti-adherent effect against DNA viruses, but were neutral against RNA viruses.

TABLE 2

Compounds and Percent Reductions and Logarithmic Reductions of RNA viruses according to High Throughput Test to Quantify the Attachment of Phage to a Surface

| # | Compound Type | Compound Name (Manufacturer) | Con. Wt. %* | INCI Name | MS2 Percent Reduct. (%) | MS2 Log R (PFU/mL) compared to growth controls | T-Test Value | Statistical Signif. e(p < 0.05) |
|---|---|---|---|---|---|---|---|---|
| 1 | Synthetic Polymer | Deposilk Q1 (Air Products and Chemicals, Inc.) | 5 | Polyquaternium-101 | 74.73 | 0.60 | 0 | S |
| 2 | Synthetic Polymer | Allianz OPT (Ashland Inc.) | 2 | Acrylates/C12-22 Alkylmethacrylate Copolymer | 7.04 | 0.03 | 0.44 | NS |

TABLE 2-continued

Compounds and Percent Reductions and Logarithmic Reductions of RNA viruses according to High Throughput Test to Quantify the Attachment of Phage to a Surface

| # | Compound Type | Compound Name (Manufacturer) | Con. Wt. %* | INCI Name | MS2 Percent Reduct. (%) | MS2 Log R (PFU/mL) compared to growth controls | T-Test Value | Statistical Signif. e(p < 0.05) |
|---|---|---|---|---|---|---|---|---|
| 3 | Synthetic Polymer | Carbopol ® Aqua SF-1 (Lubrizol Corporation) | 2 | Acrylates Copolymer | 66.48 | 0.47 | 0.03 | S |
| 4 | Synthetic Polymer | Lexorez ® 200 (Inolex) | 5 | Trimethylpentanediol/ Adipic Acid/Glycerin Crosspolymer | 70.06 | 0.52 | 0.04 | S |
| 5 | Synthetic Polymer | Lexorez ® TL-8 (Inolex) | 5 | Trimethylpentanediol/ Adipic Acid Copolymer | 67.65 | 0.49 | 0.01 | S |
| 6 | Synthetic Polymer | Pluronic ® 85 (BASF Corporation) | 5 | Ethylene Oxide/Propylene Oxide Block Copolymer | 37.28 | 0.20 | 0.12 | NS |
| 7 | Cosmetic Oil (Ester) | Cetiol ® 868 (BASF Corporation) | 100 | Ethylhexyl Stearate | 87.46 | 0.90 | 0 | S |
| 8 | Cosmetic Oil (Ester) | Escalo ®l 587 (Ashland Inc.) | 100 | Ethylhexyl Salicylate | 85.40 | 0.84 | 0 | S |
| 9 | Cosmetic Oil (Ester) | Escalol ® 597 (Ashland Inc.) | 100 | Octocrylene | −30.27 | −0.11 | 0.38 | NS |

*Con. Wt. % = Concentration of Compound in 5% glycerin and QS water, by total weight of solution, unless compound was tested at 100% concentration

TABLE 3

Compounds and Percent Reductions and Logarithmic Reductions of DNA viruses according to High Throughput Test to Quantify the Attachment of Phage to a Surface

| # | Compound Type | Compound Name (Manufacturer) | Con. Wt. %* | INCI Name | Phi X 174 Percent Reduct. (%) | Phi X 174 Log. R (PFU/mL) compared to growth controls | T-Test Value | Statistical Signif. e(p < 0.05) |
|---|---|---|---|---|---|---|---|---|
| 1 | Synthetic Polymer | Deposilk Q1 (Air Products and Chemicals, Inc.) | 5 | Polyquaternium-101 | 12.97 | 0.06 | 0.31 | NS |
| 2 | Synthetic Polymer | Allianz OPT (Ashland Inc.) | 2 | Acrylates/C12-22 Alkylmethacrylate Copolymer | 82.21 | 0.75 | 0 | S |
| 3 | Synthetic Polymer | Carbopol ® Aqua SF-1 (Lubrizol Corporation) | 2 | Acrylates Copolymer | 81.69 | 0.74 | 0 | S |
| 4 | Synthetic Polymer | Lexorez ® 200 (Inolex) | 5 | Trimethylpentanediol/ Adipic Acid/Glycerin Crosspolymer | 94.70 | 1.28 | 0 | S |
| 5 | Synthetic Polymer | Lexorez ® TL-8 (Inolex) | 5 | Trimethylpentanediol/ Adipic Acid Copolymer | 87.85 | 0.92 | 0 | S |
| 6 | Synthetic Polymer | Pluronic ® 85 (BASF Corporation) | 5 | Ethylene Oxide/Propylene Oxide Block Copolymer | 93.91 | 1.22 | 0 | S |
| 7 | Cosmetic Oil (Ester) | Cetiol ® 868 (BASF Corporation) | 100 | Ethylhexyl Stearate | 98.58 | 1.85 | 0 | S |
| 8 | Cosmetic Oil (Ester) | Escalo ®l 587 (Ashland Inc.) | 100 | Ethylhexyl Salicylate | 91.45 | 1.07 | 0 | S |

TABLE 3-continued

Compounds and Percent Reductions and Logarithmic Reductions of DNA viruses according to High Throughput Test to Quantify the Attachment of Phage to a Surface

| # | Compound Type | Compound Name (Manufacturer) | Con. Wt. %* | INCI Name | Phi X 174 Percent Reduct. (%) | Phi X 174 Log. R (PFU/mL) compared to growth controls | T-Test Value | Statistical Signif. e(p < 0.05) |
|---|---|---|---|---|---|---|---|---|
| 9 | Cosmetic Oil (Ester) | Escalol ® 597 (Ashland Inc.) | 100 | Octocrylene | 93.44 | 1.18 | 0 | S |

*Con. Wt. % = Concentration of Compound in 5% glycerin and QS water, by total weight of solution, unless compound was tested at 100% concentration

TEST METHODS

High Throughput Attachment Test Method

This test method specifies the operational parameters required to grow and or prevent the formation of bacterial attachment using a high throughput screening assay. The assay device consists of a plastic lid with ninety-six (96) pegs and a corresponding receiver plate with ninety-six (96) individual wells that have a maximum 200 µL working volume. Biofilm is established on the pegs under static batch conditions (i.e., no flow of nutrients into or out of an individual well).
1. Terminology
  1.2 Definitions of Terms Specific to This Standard:
  1.2.2 peg, n—biofilm sample surface (base: 5.0 mm, height: 13.1 mm).
  1.2.3 peg lid, n—an 86×128 mm plastic surface consisting of ninety-six (96) identical pegs.
  1.2.4 plate, n—an 86×128 mm standard plate consisting of ninety-six (96) identical wells.
  1.2.5 well, n—small reservoir with a 50 to 200 µL working volume capacity.
2. Acronyms
  2.2 ATCC: American Type Culture Collection
  2.3 CFU: colony forming unit
  2.4 rpm: revolutions per minute
  2.5 SC: sterility control
  2.6 TSA: tryptic soy agar
  2.7 TSB: tryptic soy broth
  2.8 GC: growth control
3. Apparatus
  3.2 Inoculating loop—nichrome wire or disposable plastic.
  3.3 Petri dish—large labelled (100×150×15 mm, plastic, sterile) for plating.
  3.4 Microcentrifuge tubes—sterile, any with a 1.5 mL volume capacity.
  3.5 96-well microtiter plate—sterile, 86×128 mm standard plate consisting of ninety-six (96) identical flat bottom wells with a 200 µL working volume
  3.6 Vortex—any vortex that will ensure proper agitation and mixing of microfuge tubes.
  3.7 Pipette—continuously adjustable pipette with volume capability of 1 mL.
  3.8 Micropipette—continuously adjustable pipette with working volume of 10 µL-200 µL.
  3.9 Sterile pipette tips—200 µL and 1000 µL volumes.
  3.10 Sterile reagent reservoir—50 mL polystyrene.
  3.11 Sterilizer—any steam sterilizer capable of producing the conditions of sterilization.
  3.12 Colony counter—any one of several types may be used. A hand tally for the recording of the bacterial count is recommended if manual counting is done.
  3.13 Environmental incubator—capable of maintaining a temperature of 35±2° C. and relative humidity between 35 and 85%.
  3.14 Reactor components—the MBEC Assay device available from Innovotech, Edmonton, AB, Canada.
  3.15 Sterile conical tubes—50 mL, used to prepare initial inoculum.
  3.16 Appropriate glassware—as required to make media and agar plates.
  3.17 Erlenmeyer flask—used for growing broth inoculum.
  3.18 Positive Displacement pipettes capable of pipetting 200 µL.
  3.19 Sterile pipette tips appropriate for Positive Displacement pipettes.
4. Reagents and Materials
  4.2 Purity of water—all references to water as diluent or reagent shall mean distilled water or water of equal purity.
  4.3 Culture media:
  4.4 Bacterial growth broth—Tryptic soy broth (TSB) prepared according to manufacturer's directions.
  4.5 Bacterial plating medium—Tryptic soy agar (TSA) prepared according to manufacturer's directions.
  4.6 Phosphate Buffered Saline (PBS)—
  4.7 Rinse Solution: Sterile PBS and TWEEN 80 (Sigma-Aldrich, St. Louis, Mo. 1% w/v.
5. MICROORGANISMS:
  5.1 *E. coli* ATCC 11229 and *S. aureus* ATCC 6538
6. TEST METHOD overview: The experimental process for the High-Throughput Anti-Adherence Test Method. This standard protocol may be broken into a series of small steps, each of which is detailed in the sections below.
  6.1 Culture Preparation
  6.1.1 *E. coli* ATCC 11229 and *S. aureus* ATCC 6538 are the organisms used in this test.
  6.1.2 Using a cryogenic stock (at −70° C.), streak out a subculture of the above listed microorganisms on organism's specific agar (TSA).
  6.1.3 Incubate at 35±2° C. for the period of time of 22±2 hours.
  6.1.4 Aseptically remove isolated colony from streak plate and inoculate 20 mL of sterile TSB.
  6.1.5 Incubate flask at 35±2° C. and 175±10 rpm for 16 to 18 hours (*E. coli* and *S. aureus*). Viable bacterial density should be $10^9$ CFU/mL and should be checked by serial dilution and plating.
  6.1.6 Pipette 10 mL from the incubation flask of *E. coli* and *S. aureus* into a 50 mL conical tube and spin down at 5 minutes at 4,000×g. Then remove supernatant and Resuspend in 10 mL sterile PBS. Approximate cell density should be $10^7$-$10^9$ CFU/mL. Vortex the sample for approximately 30 seconds to achieve a homogeneous distribution of cells.

6.1.7 Perform 10-fold serial dilutions of the inoculum in triplicate.

6.1.8 Plate appropriate dilutions on appropriately labelled TSA plates. Incubate the plates at 35±2° C. for 22±2 hours depending on the isolates growth rate and enumerate.

6.2 Preparation of the Challenge plates:

6.2.1 Preparation of compounds and coating compounds onto MBEC plate lid 6.2.1.1.1 Using a positive displacement pipette aseptically add 200 µL of compounds and control to be tested to a sterile 96-well microplate according to the plate layout of Table 4 below.

TABLE 4

Sample layout of 96-well MBEC plate.

| | 1 | 2 | 3 | 4 | 5 | 6 | 7 | 8 | 9 | 10 | 11 | 12 |
|---|---|---|---|---|---|---|---|---|---|---|---|---|
| E. coli | A | AC | T1 | T2 | T3 | T4 | T5 | T6 | T7 | T8 | NT-GC | T1-SC |
| E. coli | B | AC | T1 | T2 | T3 | T4 | T5 | T6 | T7 | T8 | NT-GC | T2-SC |
| E. coli | C | AC | T1 | T2 | T3 | T4 | T5 | T6 | T7 | T8 | NT-GC | T3-SC |
| E. coli | D | AC | T1 | T2 | T3 | T4 | T5 | T6 | T7 | T8 | NT-GC | T4-SC |
| S. aureus | E | AC | T1 | T2 | T3 | T4 | T5 | T6 | T7 | T8 | NT-GC | T5-SC |
| S. aureus | F | AC | T1 | T2 | T3 | T4 | T5 | T6 | T7 | T8 | NT-GC | T6-SC |
| S. aureus | G | AC | T1 | T2 | T3 | T4 | T5 | T6 | T7 | T8 | NT-GC | T7-SC |
| S. aureus | H | AC | T1 | T2 | T3 | T4 | T5 | T6 | T7 | T8 | NT-GC | T8-SC |

AC = Attachment Control
NT-GC = No Treatment Growth Control
SC = Sterility Control
T1-T8 = Test Codes 6.2.1.1.2 Add 200 µL of each code to the appropriate well for sterility controls.

6.2.1.1.3 Place the MBEC plate lid, peg side down into the 96-well microplate containing the test compound solutions.

6.2.1.1.4 Allow the plate to sit at room temperature (25±3° C.) for 2 hours.

6.2.1.1.5 Remove the MBEC plate lid and allow the lid to dry at room temperature (25±3° C.) overnight in a laminar flow hood.

7.1 Bacterial Adherence Challenge:

7.1.1 Add 100 µL of diluted bacteria to the appropriate wells in a sterile 96-well microplate as indicated in the plate layout in Table 4.

7.1.2 Add 200 µL of sterile PBS to the sterility controls.

7.1.3 The MBEC containing dried compounds is then inserted into the bacterial inoculated 96 well flat bottom microplate from section 9.3.1

7.1.4 Incubate stationary at room temperature (25±3° C.) for 15 minutes.

7.1.5 Remove the MBEC lid and place into a 96-well microplate containing 200 µL PBS+1% w/v TWEEN 80. Incubate stationary at room temperature (25±3° C.) for 15 seconds.

7.1.6 Repeat step 7.1.5 for two additional washes for a total of 3 washes.

7.2 Method to Determine Number of Attached Bacteria 7.2.1 Transfer the washed MBEC plate lid to a 96-well plate containing 200 µL ALAMARBLUE reagent (prepared according to manufacturer's directions, Life Technologies, Carlsbad, Calif.) in each well to be tested.

7.2.2 The final plate is transferred to a SPECTRAMAX GEMINI EM microplate reader (Molecular Devices, Inc. Sunnyvale, Calif. USA) for a 20 hour kinetic, bottom read with an excitation of 560 nm and emission of 590 nm. The rate of fluorescence development (relative fluorescence units (RFU)/minute) is determined for each well.

7.2.3 From these data, the ratio of bacterial growth on the test codes pegs to the bacterial growth on the nontreated growth control pegs was calculated.

If the ratio of bacterial growth on the test code pegs to the bacterial growth on the nontreated growth control pegs is less than 85%, the agent is deemed to be anti-adherent;

If the ratio of bacterial growth on the test code pegs to the bacterial growth on the nontreated growth control pegs is between 85%-115%, the agent is deemed to be neutral (neither adherent nor anti-adherent); and If the ratio of bacterial growth on the test code pegs to the bacterial growth on the nontreated growth control pegs is greater than 115%, the agent is deemed to be adherent.

HIGH THROUGHPUT TEST TO QUANTIFY THE ATTACHMENT OF PHAGE TO A SURFACE 1.0 Test Methods:

Growth and purification of phage is outlined in the following steps.

1.1 Subculture: (these steps ensured that the organism are less than 5 generations removed from the original clinical isolate):

1.1.1 Using a cryogenic stock (at −70° C.), a first subculture of the bacterial organisms listed above is streaked out on appropriate media.

1.1.2 The plate is incubated at 36±2° C. for 24 hours and store the plate is wrapped in parafilm at 4° C.

1.1.3 From the first sub-culture, a second sub-culture is streaked out on appropriate media. It is incubated at 36±2° C. for 24 hours. The second sub-culture is used within 24 hours starting from the time it is first removed from incubation.

1.1.4 Organism(s) from the second sub-culture are inoculated into 30-200 mL OSB and incubated at 36±2° C. on a rotary shaker (at approximately 150 rpm) for 16-18 hours. This is to achieve an inoculum density of approximately $10^9$ CFU/ml.

1.2 Prepare Top Agar:

1.2.1 Top Agar is prepared by preparing 200 mL of OSB according to manufacturer's directions and adding 0.7% agar. After sterilization, the sterilized mix is stored in a water bath set at 49° C.

1.2.2 The top agar solution is aliquoted by moving 4 mL into sterile tubes. The tubes are kept at 49 C until needed for use.

1.3 Preparation of bacterial host:

1.3.1 40 mL of broth culture is moved to a centrifuge tube.

1.3.2 The overnight broth culture is centrifuged at 4000×g for 5 minutes.

1.3.3 The supernatant is decanted and the cells were re-suspended in the same volume (40 mL for example) of BPB.

1.3.4 Steps 4.2.2 to 4.2.3 are repeated one more time.

1.4 Propagation of the Phage:

1.4.1 The OSA plates to be used are warmed to room temperature.

1.4.2 The top agar tubes are inoculated with 200 μL of concentrated phage stock from either an ATCC or a previously stored concentrated stock. For frozen stock 500 μL of TSB warmed to 49° C. is added before adding to the Top Agar.

1.4.3 100 μL of the washed broth culture is added and swirled gently to mix.

1.4.4 Each inoculated top agar tube is poured onto one prepared OSA plate. The plate is tilted to ensure that the top agar was spread across the entire surface.

1.4.5 The top agar is allowed to solidify, was inverted and placed in an incubator at 37° C. for overnight growth.

1.4.6 Following overnight growth the plates should show complete clearing.

1.4.7 The SM Buffer solution is warmed to 49° C.

1.4.8 2 mL of warmed SM Buffer is added to each plate and the top agar is scraped using sterile white Teflon policeman. A pipette is used to transfer all the SM buffer and top agar to a sterile tube. This is done for every plate.

1.4.9 The collected top agar tubes are vortexed for 10-15 seconds.

1.4.10 The vortexed tubes are centrifuged at 1000×g for 25 minutes.

1.4.11 From each centrifuged tube the supernatants are pooled in one new sterile tube.

1.4.12 A sterile 0.20 filter is prepared by flushing 2-3 mL of 3% w/v cold (4C) beef extract through the filter and discarded.

1.4.13 The prepared filter is used to filter the pooled recovered top agar into a fresh sterile tube.

1.4.14 The collected filtrate is the purified phage. Plaque Forming Units (PFU) are checked by serially diluting and spot plating using the method described in section 4.5.

1.5 Phage (MS2 and PhiX 174) Enumeration:

1.5.1 Phage is prepared for use from the stock by diluting 1:1 in BPB.

1.5.2 Spot Plate Method:

1.5.2.1 A cell dilution of ~$10^6$ CFU/mL of *E. coli* (*E. coli* K12 is used for MS2 phage and *E. coli* C is used for PhiX 174) is prepared from the prepared washed broth culture by diluting in sterile BPB.

1.5.2.2 An inoculum check is performed on the bacterial dilution in triplicate.

1.5.2.3 In a 96 well plate, columns 1-12 are filled with 180 μL of the $10^6$ CFU/ml *E. coli* suspension in BPB 1.5.2.4 20 μL of the samples to be diluted is added in column 1.

1.5.2.5 10-fold (10×Dilution) in BPB is performed from $10^1$-$10^{12}$ by moving 20 μL from column 1 to column 2 and mixing. This is repeated, moving down the columns until column 12.

1.5.2.6 20 μL (or 10 if agar permits) is spot plated on a large labelled OSA plate (spot plate every second column to avoid cross merging of spot plated phages.

1.5.2.7 Plates are inverted & incubated for 24 h at 37° C.

1.5.2.8 After 24 h the number of PFU is counted.

1.6 Preparation of the Challenge plates:

TABLE 5

The challenge will be tested using the specified contact time (Total of 6 challenge plates).

| | 1 | 2 | 3 | 4 | 5 | 6 | 7 | 8 | 9 | 10 | 11 | 12 |
|---|---|---|---|---|---|---|---|---|---|---|---|---|
| A | A | B | C | D | E | F | | | | SC-A | GC | GC |
| B | A | B | C | D | E | F | | | | SC-B | GC | GC |
| C | A | B | C | D | E | F | | | | SC-C | GC | GC |
| D | A | B | C | D | E | F | | | | SC-D | GC | GC |
| E | A | B | C | D | E | F | | | | SC-E | GC | GC |
| F | A | B | C | D | E | F | | | | SC-F | GC | GC |
| G | A | B | C | D | E | F | | | | | GC | GC |
| H | A | B | C | D | E | F | | | | | GC | GC |

SC = sterility control wells
GC = growth control wells 1.6.1 Preparation of compounds and coating compounds onto MBEC plate lid 1.6.2 Using a positive displacement pipette aseptically add 200 μL of compounds to be tested to a sterile 96-well microplate according to the plate layout described below.

1.6.3 Add 200 μL of each code to the appropriate well for sterility controls.

1.6.4 Place the MBEC plate lid, peg side down into the 96-well microplate containing the test compound solutions.

1.6.5 Allow the plate to sit at room temperature (25±3° C.) for 2 hrs.

1.6.6 Remove the MBEC plate lid and allow the lid to dry at room temperature (25±3° C.) overnight in a laminar flow hood by spacing the MBEC plate lid from the MBEC plate trough with two 10 μL disposable loops.

1.7 Phage attachment to MBEC Lids:

1.7.1 Using the phage prepared in 1:1 BPB from stock 100 μL is added to the wells indicated by the plate layout of the sterile 96 well plate.

1.7.2 The sterile MBEC lid is placed into the wells.

1.7.3 The plate is allowed to incubate for 1 hour at room temperature without shaking.

1.7.4 Rinse plates, 3 plates per MBEC lid, by adding 200 μL of PBS to wells indicated by the plate layout of a sterile 96 well plate.

1.8 Phage Recovery:

1.8.1 Using flamed pliers the pegs are removed from the MBEC lid and placed in a tube containing 5 mL BPB.

1.8.2 Vortex for 1 minute.

1.8.3 Perform a serial dilution on the recovery solution.

1.8.4 Enumerate the PFU by using one of the methods indicated previously.

1.9 $LOG_{10}$ Reduction:

1.9.1 In a 96 well plate, columns 1-12 are filled with 180 μL of the 10E6 CFU/ml of the appropriate *E. coli* suspension in BPB 1.9.2 20 μL of the samples to be diluted is added in column 1.

1.9.3 10-fold (10×Dilution) in BPB is performed from 10E1-10e12 by moving 20 μL from column 1 to column 2 and mixing. This is repeated, moving down the columns until column 12.

1.9.4 20 μL (or 10 if agar permits) is spot plated on a large labelled OSA plate (spot plate every second column to avoid cross merging of spot plated phages.

1.9.5 Plates are inverted & incubated for 24 h at 37° C.

1.9.6 After 24 h the number of PFU is counted.

1.9.7 Cell Enumeration:
1.9.7.1 Count the appropriate number of colonies according to the plating method used.
1.9.7.2 Calculate the arithmetic mean of the colonies counted on the plates.

The log density for one peg is calculated as follows:

$$LOG_{10}(PFU/peg)=LOG_{10}[(X/B)(D)] \text{ where:}$$

X=mean PFU,
B=volume plated (0.02 mL)
and D=dilution.

Calculate the overall attached bacteria accumulation by calculating the mean of the log densities calculated.

Calculate the $LOG_{10}$ reduction for each dilution as follows: $LOG_{10}$ Reduction=Mean $LOG_{10}$ Growth Control–Mean $LOG_{10}$ Test.

Calculate the Percent Reduction by calculating ($Log_{10}$ (PFU/Peg) of the growth control pegs–$Log_{10}$(PFU/Peg) of the treated pegs)/$Log_{10}$(PFU/Peg) of the growth control pegs)×100

1.10 Accept or Reject Criteria
1.10.1 Growth controls for the phage are between 4 and 6 $Log_{10}$
1.10.2 Sterility controls do not show any growth.

EMBODIMENTS

Embodiment 1: A method of inhibiting microbes from attaching to a surface, the method comprising: providing an anti-adherent composition, the anti-adherent composition comprising: an anti-adherent agent configured to inhibit microbes from attaching to the surface, the anti-adherent agent selected from the group consisting of: Acrylates Copolymer, Trimethylpentanediol/Adipic Acid/Glycerin crosspolymer, Trimethylpentanediol/Adipic Acid Copolymer, Ethylhexyl Stearate, Ethylhexyl Salicylate, Acrylates/C12-22 Alkylmethacrylate Copolymer, Octocrylene, Ethylene Oxide/Propylene Oxide Block Copolymer, and Polyquaternium-101, and any combinations thereof; applying the composition to the surface; and allowing at least some of the composition to remain on the surface such that the anti-adherent agent inhibits microbes from attaching to the surface.

Embodiment 2: The method of embodiment 1, wherein the composition further comprises a humectant.

Embodiment 3: The method of embodiment 2, wherein the humectant is selected from the group consisting of: glycerin, a glycerin derivative, and combinations thereof.

Embodiment 4: The method of any one of the preceding embodiments, wherein the composition further comprises an ingredient selected from the group consisting of an emollient, a surfactant, an antimicrobial agent, and any combination thereof.

Embodiment 5: The method of any one of the preceding embodiments, wherein the composition is non-antimicrobial.

Embodiment 6: The method of any one of the preceding embodiments, wherein the microbes comprise Gram negative bacteria, and the anti-adherent agent is selected from the group consisting of: Acrylates Copolymer, Trimethylpentanediol/Adipic Acid Copolymer, and Ethylhexyl Stearate.

Embodiment 7: The method of any one of embodiments 1-5, wherein the microbes comprise Gram positive bacteria, and the anti-adherent agent is selected from the group consisting of: Acrylates Copolymer, Ethylhexyl Stearate, Ethylhexyl Salicylate, Acrylates/C12-22 Alkylmethacrylate Copolymer, Octocrylene, and Ethylene Oxide/Propylene Oxide Block Copolymer.

Embodiment 8: The method of any one of embodiments 1-5, wherein the microbes comprise a DNA virus, and the anti-adherent agent is selected from the group consisting of: Acrylates Copolymer, Trimethylpentanediol/Adipic Acid/Glycerin crosspolymer, Trimethylpentanediol/Adipic Acid Copolymer, Ethylhexyl Stearate, Ethylhexyl Salicylate, Acrylates/C12-22 Alkylmethacrylate Copolymer, Octocrylene, and Ethylene Oxide/Propylene Oxide Block Copolymer.

Embodiment 9: The method of any one of embodiments 1-5, wherein the microbes comprise an RNA virus, and the anti-adherent agent is selected from the group consisting of: Acrylates Copolymer, Trimethylpentanediol/Adipic Acid/Glycerin crosspolymer, Trimethylpentanediol/Adipic Acid Copolymer, Ethylhexyl Stearate, Ethylhexyl Salicylate, and Polyquaternium-101.

Embodiment 10: An anti-adherent composition for preventing microbes from attaching to a surface, the anti-adherent composition comprising: an anti-adherent agent selected from the group consisting of: Trimethylpentanediol/Adipic Acid/Glycerin crosspolymer, Trimethylpentanediol/Adipic Acid Copolymer, Ethylhexyl Stearate, and Acrylates/C12-22 Alkylmethacrylate Copolymer, and any combinations thereof; and a humectant.

Embodiment 11: The anti-adherent composition of embodiment 10, wherein the humectant is selected from the group consisting of: glycerin, glycerin derivatives, hyaluronic acid derivatives, betaine derivatives amino acids, amino acid derivatives, glycosaminoglycans, glycols, polyols, sugars, sugar alcohols, hydrogenated starch hydrolysates, hydroxy acids, hydroxy acid derivatives, salts of PCA, and any combination thereof.

Embodiment 12: The anti-adherent composition of embodiment 10, wherein the humectant is selected from the group consisting of: honey, sorbitol, hyaluronic acid, sodium hyaluronate, betaine, lactic acid, citric acid, sodium citrate, glycolic acid, sodium glycolate, sodium lactate, urea, propylene glycol, butylene glycol, pentylene glycol, ethoxydiglycol, methyl gluceth-10, methyl gluceth-20, PEG-2, PEG-3, PEG-4, PEG-5, PEG-6, PEG-7, PEG-8, PEG-9, PEG-10, xylitol, maltitol, and any combination thereof.

Embodiment 13: The anti-adherent composition of embodiment 10, wherein the humectant is selected from the group consisting of: glycerin, a glycerin derivative, and combinations thereof.

Embodiment 14: The anti-adherent composition of any one of embodiments 10-13, wherein the composition further comprises an ingredient selected from the group consisting of an emollient, a surfactant, an antimicrobial agent, and any combination thereof.

Embodiment 15: The anti-adherent composition of any one of embodiments 10-14, wherein the composition is non-antimicrobial.

Embodiment 16: The anti-adherent composition of any one of embodiments 10-15, wherein the anti-adherent agent is present in the amount of about 0.01% to about 20.0% by weight of the composition, and wherein the humectant is present in the amount of about 0.01% to about 20.0% by weight of the composition.

Embodiment 17: An anti-adherent composition for preventing microbes from attaching to a surface, the anti-adherent composition comprising: an anti-adherent agent selected from the group consisting of: Acrylates Copolymer, Trimethylpentanediol/Adipic Acid/Glycerin Crosspolymer, Trimethylpentanediol/Adipic Acid Copolymer, Ethylhexyl Stearate, Ethylhexyl Salicylate, Acrylates/C12-22 Alkylmethacrylate Copolymer, and Polyquaternium-101, and any combinations thereof; and a humectant; wherein the anti-adherent composition is non-antimicrobial.

Embodiment 18: The anti-adherent composition of embodiment 17, wherein the humectant is selected from the group consisting of: glycerin, a glycerin derivative, and combinations thereof.

Embodiment 19: The anti-adherent agent composition of embodiment 17 or 18, wherein the anti-adherent agent is present in the amount of about 0.01% to about 20.0% by weight of the composition, and wherein the humectant is present in the amount of about 0.01% to about 20.0% by weight of the composition.

Embodiment 20: A wipe for inhibiting the attachment of microbes to a surface, the wipe comprising: a nonwoven substrate; and the anti-adherent composition according to any one of embodiments 10-19.

When introducing elements of the present disclosure, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the disclosure.

What is claimed is:

1. A method of inhibiting microbes from attaching to a surface, the method comprising:
   providing an anti-adherent composition, the anti-adherent composition comprising:
      an anti-adherent agent configured to inhibit microbes from attaching to the surface, the anti-adherent agent selected from the group consisting of: Trimethylpentanediol/Adipic Acid/Glycerin crosspolymer, Trimethylpentanediol/Adipic Acid Copolymer, Ethylhexyl Stearate, Ethylhexyl Salicylate, Acrylates/C12-22 Alkylmethacrylate Copolymer, and Octocrylene, and any combinations thereof, wherein the composition is non-antimicrobial;
   applying the composition to the surface; and
   allowing at least some of the composition to remain on the surface such that the anti-adherent agent inhibits microbes from attaching to the surface.

2. The method of claim 1, wherein the composition further comprises a humectant.

3. The method of claim 2, wherein the humectant is selected from the group consisting of: glycerin, a glycerin derivative, and combinations thereof.

4. The method of claim 1, wherein the composition further comprises an ingredient selected from the group consisting of an emollient, a surfactant, and any combination thereof.

5. The method of claim 1, wherein the microbes comprise Gram negative bacteria, and the anti-adherent agent is selected from the group consisting of: Trimethylpentanediol/Adipic Acid Copolymer and Ethylhexyl Stearate.

6. The method of claim 1, wherein the microbes comprise Gram positive bacteria, and the anti-adherent agent is selected from the group consisting of: Ethylhexyl Stearate, Ethylhexyl Salicylate, Acrylates/C12-22 Alkylmethacrylate Copolymer, and Octocrylene.

7. The method of claim 1, wherein the microbes comprise a DNA virus, and the anti-adherent agent is selected from the group consisting of: Trimethylpentanediol/Adipic Acid/Glycerin crosspolymer, Trimethylpentanediol/Adipic Acid Copolymer, Ethylhexyl Stearate, Ethylhexyl Salicylate, Acrylates/C12-22 Alkylmethacrylate Copolymer, and Octocrylene.

8. The method of claim 1, wherein the microbes comprise an RNA virus, and the anti-adherent agent is selected from the group consisting of: Trimethylpentanediol/Adipic Acid/Glycerin crosspolymer, Trimethylpentanediol/Adipic Acid Copolymer, Ethylhexyl Stearate, and Ethylhexyl Salicylate.

9. The method of claim 1, wherein the anti-adherent agent is present in an amount of at least about 0.10% by weight of the composition.

10. The method of claim 1, wherein the anti-adherent agent is present in an amount from about 0.10% to about 20% by weight of the composition.

\* \* \* \* \*